United States Patent
Panchal et al.

(10) Patent No.: US 10,941,105 B1
(45) Date of Patent: Mar. 9, 2021

(54) METHOD FOR DIRECT CONVERSION OF CARBON DIOXIDE TO DIALKYL CARBONATES USING ETHYLENE OXIDE AS FEEDSTOCK

(71) Applicant: E3TEC SERVICE, LLC, Hoffman Estates, IL (US)

(72) Inventors: Chandrakant B. Panchal, South Barrington, IL (US); Richard Doctor, Lisle, IL (US)

(73) Assignee: E3Tec Service, LLC, Hoffman Estates, IL (US)

( * ) Notice: Subject to any disclaimer, the term of this patent is extended or adjusted under 35 U.S.C. 154(b) by 0 days.

(21) Appl. No.: 15/929,808

(22) Filed: May 22, 2020

Related U.S. Application Data

(60) Provisional application No. 62/852,614, filed on May 24, 2019.

(51) Int. Cl.
*C07C 68/04* (2006.01)
*C07C 68/08* (2006.01)
*B01D 3/06* (2006.01)
*B01J 8/18* (2006.01)
*B01D 5/00* (2006.01)
*B01J 8/00* (2006.01)
*B01D 3/32* (2006.01)

(52) U.S. Cl.
CPC ............. *C07C 68/04* (2013.01); *B01D 3/06* (2013.01); *B01D 3/322* (2013.01); *B01D 5/006* (2013.01); *B01J 8/009* (2013.01); *B01J 8/1818* (2013.01); *C07C 68/08* (2013.01)

(58) Field of Classification Search
CPC .............................. C07C 68/04; C07C 68/08
See application file for complete search history.

(56) References Cited

U.S. PATENT DOCUMENTS

2013/0225840 A1* 8/2013 Zhang ................. C07D 317/38
549/230

* cited by examiner

*Primary Examiner* — Shawquia Jackson
(74) *Attorney, Agent, or Firm* — Rosenberg, Klein & Lee

(57) ABSTRACT

A method for co-production of high purity dimethyl carbonate and mono-ethylene glycol by applying a reactor, such as a membrane reactor and/or an adsorbent-catalytic reactor by capturing and reacting carbon dioxide with methanol and ethylene oxide. Carbon dioxide may be recovered from primary sources (utilities and industrial processes) by a membrane or solid adsorbent, and subsequently converted to an intermediate hydroxy-ethyl-methyl carbonate by reacting with ethylene oxide and methanol. For high-purity carbon dioxide (obtained by carbon capture technologies or from an ethanol fermentation process), the membrane reactor is replaced with a catalytic reactor for direct conversion of carbon dioxide to hydroxy-ethyl-methyl carbonate by reacting with ethylene oxide and methanol. The hydro-ethyl-methyl carbonate is further reacted with methanol for conversion to dimethyl carbonate. A combination of heterogeneous and homogeneous catalysts is implemented for an effective conversion of carbon dioxide. An integrated reactive distillation process using side reactors is used for facilitating catalytic reaction for production of high purity dimethyl carbonate.

20 Claims, 13 Drawing Sheets

METHOD FOR DIRECT CONVERSION OF CARBON DIOXIDE TO DIALKYL CARBONATES USING ETHYLENE OXIDE AS FEEDSTOCK

STATEMENT REGARDING FEDERAL SPONSORED RESEARCH OR DEVELOPMENT

This invention is made with government support under DE-SC0013233 awarded by the U.S. Department of Energy. The government has certain rights in the invention.

REFERENCE TO RELATED APPLICATIONS

This Utility Patent Application is based upon Provisional Patent Application No. 62/852,614 filed on 24 May 2019.

INCORPORATION BY REFERENCE

U.S. Pat. No. 9,518,003 is incorporated herein by reference.

FIELD OF THE INVENTION

The subject invention is directed to a process for synthesis of alkyl carbonates, and particularly, to production of dimethyl carbonate (DMC) from hydroxy-ethyl-methyl-carbonate (HEMC) by a direct reaction of carbon dioxide with ethylene oxide and methanol.

The subject invention is also directed to a process for synthesis of DMC from HEMC by employing either a membrane reactor or a solid adsorbent reactor for recovery and conversion of carbon dioxide from a primary source to HEMC, or, alternatively, using a catalytic reactor for reacting high-purity carbon dioxide (captured in a commercial process, for example, the amine process, or ethanol fermentation process) to high-purity dimethyl carbonate.

The subject invention is further directed to the synthesis of dimethyl carbonate (DMC) which integrates a membrane reactor and/or a solid adsorbent reactor in the synthesis process, where the membrane reactor continuously captures carbon dioxide from primary sources, wherein the captured carbon dioxide diffuses through the membrane surface and reacts with flowing ethylene oxide and methanol to form HEMC. In addition, the adsorbent reactor, which is loaded with a solid adsorbent and conversion catalysts, operates in a cyclic manner by initially capturing carbon dioxide from primary sources by a solid adsorbent until it is nearly saturated. Subsequently, ethylene oxide and methanol reactants are fed to the adsorbent reactor for reacting with adsorbed carbon dioxide to form hydroxyl-ethyl-methyl carbonate. The simultaneous carbon dioxide capture from the primary sources of carbon dioxide (that are preferably the utility plants and industrial processes) for production of value-added dimethyl carbonate (DMC) along with coproduct mono-ethylene glycol (MEG) constitute an essential part of the subject invention.

In addition, the subject invention is directed to an improved process for synthesis of hydroxy-ethyl-methyl carbonate (an intermediate stage for production of dimethyl carbonate) which avoids a conventional process of ethylene carbonate characterized by a high energy consumption and capital costs (CAPEX).

The subject invention also addresses a process for synthesis of dimethyl carbonate which uses three heat-integrated distillation columns for achieving high-concentration of pure dimethyl carbonate with lower energy consumption and low carbon-footprint.

BACKGROUND OF THE INVENTION

Conventionally, amine-process-based recovery of carbon dioxide from a raw natural gas is practiced in a chemical reducing environment. In applications for an oxidizing environment, amine can be used for carbon dioxide recovery from combustion flue gases. In such systems, carbon dioxide is absorbed from the combustion flue gas and subsequently recovered from the rich Amine stream by stream stripping.

Emerging carbon dioxide capture technologies include: a) membrane separation; b) alternate solvents to Amines; c) solid adsorbent; and d) non-aqueous solvents (presented in the DOE/NETL Project Review Proceedings, DOE/NETL Project Review Proceedings http:/www.netl.doe.gov/events/conference-proceedings/2018/2018-netl-co2-capture-technology-project-review-meeting).

Alkyl carbonates cover a group of organic carbonates with a broad supply chain for end-use applications like "green" low-volatile solvents, as electrolytes in lithium-ion batteries, chemical intermediate for production of polyurethanes and in the expanding polycarbonate market.

Commercially, dimethyl carbonate is manufactured by reacting methanol with syngas which is produced from natural gas, petroleum products or coal gasification with high emissions of carbon dioxide. With the expanding global demands of alkyl carbonates the industry is seeking alternate synthesis processes using carbon dioxide.

Unfortunately, the conventional direct conversion of carbon dioxide to DMC using different catalysts has significant limitations, as shown, for example, by Tamboli, et al., ("Catalytic Development in the Direct Dimethyl Carbonate Synthesis from Carbon Dioxide and Methanol," Chemical Engineering Journal, 33, pp. 530-544, 2017), and Kabra, et al, ("Direct Synthesis of Dimethyl Carbonate from Methanol and Carbon Dioxide: A Thermodynamic and Experimental Study," J. of Supercritical Fluids, 117, pp. 98-107, 2016).

Thermodynamic limitations of the direct conversion of carbon dioxide to alkyl carbonates require extreme operating conditions, such as high pressure, high temperature, and critical fluid conditions. Even under such reaction conditions, the conversion is relatively low, which requires recycling a large fraction of unreacted reagents.

Unless innovative catalysts are developed for the reaction to occur at moderate conditions with high conversion rate, the direct conversion of $CO_2$ to alkyl carbonates is expected to be limited to scientific studies which are prevented from advancing to commercial plants.

Therefore, it would be desirable to develop a process using chemical carriers, such as, for example, ethylene oxide, to form an intermediate stage preceding the stage of synthesis of alkyl carbonates.

PRIOR ART

Described in U.S. Pat. No. 9,518,003, is a process for synthesis of hydroxy-ethyl-methyl carbonate by reacting ethylene carbonate with methanol. Hydroxy-ethyl-methyl carbonate is further reacted with methanol to produce dimethyl carbonate using a heat integrated reactive distillation equipped with side reactors and permeation-vaporization (PerVap) membranes for separation of azeotropic mixture of methanol and dimethyl carbonate. Ethylene carbonate is produced commercially by reacting carbon dioxide with ethylene oxide at high temperature and pressure using homogeneous catalysts (presented in U.S. Pat. No. 4,233,221).

Such a high-pressure process is not feasible for recovery and conversion of carbon dioxide from low-pressure primary sources. It is highly desirable to provide a low-pressure synthesis of hydroxy-ethyl-methyl carbonate.

Conventional direct conversion of carbon dioxide to dimethyl carbonate using different catalysts has significant limitations, as presented by Tamboli, et al. and Kabra, et al. (referenced in previous paragraphs). Thermodynamic limitations of direct conversion of carbon dioxide to alkyl carbonates require extreme operating conditions such as high pressure, high temperature and critical fluid conditions. Even under such reaction conditions the conversion is relatively low, which requires recycling of large fraction of unreacted reagents. Until novel catalysts are developed for reaction to occur at moderate conditions with high conversion, the direct conversion of carbon dioxide to alkyl carbonate is expected to be limited only to scientific studies without advancing to commercial plants. Therefore, it is essential to develop a process using chemical carrier, such as ammonia, to form an intermediate followed by synthesis of alkyl carbonates.

Significant limitations of conventional process presented in previous paragraphs are partially due to the usage of ethylene oxide or alternate carbonate followed by transesterification reaction for synthesis of alkyl carbonates. The laboratory studies have been focused on evaluating different catalysts by following the reaction path represented by Equation 1:

CH$_2$—O-CH$_2$+CO$_2$→CH$_2$O—CO—OCH$_2$ Ethylene Oxide Ethylene Carbonate

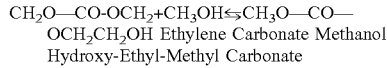
CH$_2$O—CO-OCH$_2$+CH$_3$OH⇆CH$_3$O—CO—OCH$_2$CH$_2$OH Ethylene Carbonate Methanol Hydroxy-Ethyl-Methyl Carbonate

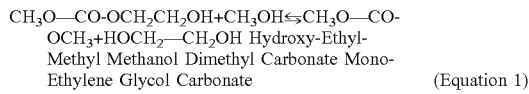
CH$_3$O—CO-OCH$_2$CH$_2$OH+CH$_3$OH⇆CH$_3$O—CO-OCH$_3$+HOCH$_2$—CH$_2$OH Hydroxy-Ethyl-Methyl Methanol Dimethyl Carbonate Mono-Ethylene Glycol Carbonate          (Equation 1)

For example, Wang et al., evaluated K$_2$CO$_3$-based binary salt in the presence of water. Dhuri et al., evaluated Amberlyst A-21 catalyst. These laboratory studies however have never transformed into a commercial process or even in pilot-plant demonstration of an integrated process. Numerous processes for synthesis of alkyl carbonates have been developed. Those includes for example: (i) Amoco, U.S. Pat. No. 5,489,703; (ii) Bayer Material Science AG, U.S. Pat. No. 8,338,631; (iii) Asahi Kasei Kogyo Kabushiki Kaisha, U.S. Pat. No. 5,847,189; and (iv) Asahi Kasei Chemicals Corporation, U.S. Pat. No. 7,645,896. Patents (i) and (ii) are not relevant to the proposed process at any level. The Asahi Patents (iii) and (vi) use side reactors. However, the Asahi's '189 Patent which uses a distillation column connected to packed-bed reactors using heterogeneous resin catalysts, have never been advanced to any improved version, nor have been implemented to practice. Asahi-Kasei's system presented '896 Patent moved away from the concept of '189 Patent based on the heterogeneous catalysts to a homogeneous catalyst reactive distillation column. The reason for refusal of further development of the system presented in '198 Patent process is believed to be that the process was not able to achieve high conversion due to slow, reversible and equilibrium-controlled reactions using side reactors.

It would be desirable to provide a process for direct conversion of carbon dioxide to alkyl carbonates using the combination of homogeneous and heterogeneous catalysts and advanced process configuration to overcome shortcomings of the Asahi's system using the heterogeneous catalyst presented in '198 Patent.

DMC and methanol form a homogeneous azeotropic mixture over a wide range of pressures which makes it difficult to separate the two components without the addition of a third component as an entrainer. It would be highly desirable to provide an efficient process that is capable of separation of DMC from other components in the system without the need for an entrainer.

SUMMARY OF THE INVENTION

It is therefore an object of the present invention to provide a process for synthesis of concentrated dimethyl carbonate which overcomes limitations of the conventional processes and obviates the need for an entrainer by employing Permeation-Vaporization (PerVap) membrane to partially break the dimethyl carbonate and methanol azeotrope.

It is a further object of the present invention to provide a process for synthesis of concentrated dimethyl carbonate which decouples a reaction distillation column from the product column, which can be operated at a higher pressure for breaking the azeotrope, where PerVap membranes with selective separation of methanol are integrated in the process. By incorporating a PerVap Membrane unit in the separation step, high-concentration DMC is produced.

In the subject process, production of concentrated dimethyl carbonate is accomplished by reacting carbon dioxide directly with ethylene oxide and methanol, thereby eliminating the high temperature commercial process of ethylene carbonate production.

Another object of the present invention is to use alternative embodiments of direct conversion of carbonate dioxide to form high purity dimethyl carbonate and mono-ethylene glycol, which include:

(a) A preferred embodiment uses a membrane reactor that captures carbon dioxide from combustion flue gases and other dilute sources. Carbon dioxide diffusing through the membrane reacts with methanol and ethylene oxide flowing on the other side of the membrane surface.

(b) A second embodiment employs a catalytic reactor for replacing the membrane reactor for relatively pure carbon dioxide captured from primary sources of combustion flue gases and other primary dilute sources.

(c) A third implementation is to capture carbon dioxide from primary sources by selective solid adsorbent, such as a metal-organic framework (MOF), nanowire adsorbent, nano particles or other solid adsorbents. The solid adsorbent chamber is loaded with suitable catalysts, such as Amberlyst A-26 or an alternate catalyst. Once the solid adsorbent is nearly saturated with carbon dioxide, the carbon dioxide source is switched to a parallel unit. Ethylene oxide and methanol reactants are fed to the solid adsorbent-catalytic reactor that was saturated with carbon dioxide facilitating a reaction that forms hydroxy-ethyl-methyl carbonate. These kinds of adsorption/desorption operations are commercially practiced in Pressure Swing Adsorption (PSA).

The resulting product stream from the afore-presented reactors consists of hydroxy-ethyl-methyl carbonate and unreacted methanol, carbon dioxide and ethylene oxide which are subsequently fed into a packed-bed catalytic reactor for further conversion. The product stream is fed into a flash tank for separating vapor and liquid phases. The vapor stream consisting of carbon dioxide and ethylene carbonate is recycled back into the packed-bed catalytic reactor.

Various commercially used and scientifically tested catalysts may be used. They may include, for example, Amberlyst A-21 and A-26, which were tested and proven qualified (Panchal C B, et al., AIChE Spring Meeting, 2018).

Additionally, the reaction may be enhanced by employing ionic catalysts, namely, tri-methyl-butyl ammonium chloride (TMBAC), tri-methyl-butyl ammonium bromide (TMBAB), tetra-butyl ammonium bromide (TBAB), tetra-butyl ammonia chloride (TBAC) and tri-ethyl-butyl ammonium bromide (TEBAB), and other similar ionic catalysts.

These ionic catalysts are soluble in methanol, and hence they may be fed in with the methanol and recovered after passing through individual direct-conversion reactors described in previous paragraphs.

The product mixture exiting from the direct conversion (catalytic, membrane or adsorbent) reactor system is fed to a catalyst recovery process which uses a heat exchanger to cool the product mixture and a flash tank for separation of vapor and liquid phases. The liquid from the flash tank is fed to a distillation column to concentrate the catalyst fraction for recycling back to the direct conversion reactor. The product stream from the catalyst recovery distillation column is fed to the first of the three columns for conversion of hydroxy-ethyl-methyl carbonate to dimethyl carbonate.

A mixture of dimethyl carbonate, hydroxy-ethyl-methyl carbonate and unreacted methanol is drawn from one of the stages of the first distillation column and passed through a side reactor thereby producing a more concentrated dimethyl carbonate composition. The product stream from the side reactor is fed to a side separation unit for separating concentrated dimethyl carbonate vapor stream and unreacted liquid stream.

The vapor streams from each of the side reactors are fed to the second column for further concentrating dimethyl carbonate. The liquid stream is then returned to the distillation column. This step is repeated for plurality of side reactor for further concentrated dimethyl carbonate.

A concentrated vapor stream of dimethyl carbonate and methanol is drawn from the top section of the first column, while the condensed stream is fed to a Permeation-Vaporization (PerVap) membrane for selective separation of methanol as the permeate stream. The retentate stream from the PerVap membrane is fed to the second column for recovery of unreacted hydroxy-ethyl-methyl carbonate for recycling to one or more of side reactors for further reaction.

The second recycling column concentrates unreacted hydroxy-ethyl-methyl carbonate as a bottom product which returns to the middle section of the first reaction column. The vapor stream from the second column is condensed and the condensed liquid stream is fed to PerVap membrane for selective separation of methanol.

The retentate from the PerVap membrane is fed to the third column, namely a product recovery column for recovery of high-concentration dimethyl carbonate as bottom product. The product recovery column is efficiently integrated with heat transfer devices to provide internal reflux in the upper section of the column and internal heating in the lower section of the column. The heat recovered from the internal reflux devices is utilized by the PerVap membrane, where such heat is required for selective vaporization of methanol. Methanol recovered from all of PerVap and the top section of the product recovery column is collected in a vessel and pumped back to side reactor as a recycle stream.

The subject invention relates to the first step of catalytic conversion of carbon dioxide to hydroxy-ethyl-methyl carbonate by reacting methanol and ethylene oxide as depicted below by chemical reaction (Equation 2).

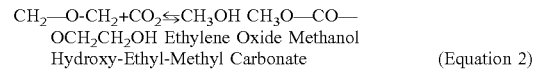
CH$_2$—O-CH$_2$+CO$_2$⇌CH$_3$OH CH$_3$O—CO—OCH$_2$CH$_2$OH Ethylene Oxide Methanol Hydroxy-Ethyl-Methyl Carbonate     (Equation 2)

Hydroxy-ethyl-methyl carbonate can be further reacted with methanol to synthesize dimethyl carbonate (DMC) and mono-ethylene glycol (MEG) as coproduct as illustrated by the second chemical reaction (Equation 3).

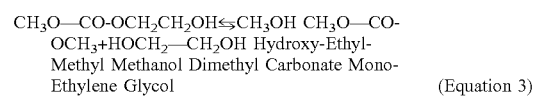
CH$_3$O—CO-OCH$_2$CH$_2$OH⇌CH$_3$OH CH$_3$O—CO-OCH$_3$+HOCH$_2$—CH$_2$OH Hydroxy-Ethyl-Methyl Methanol Dimethyl Carbonate Mono-Ethylene Glycol     (Equation 3)

This following chemical reaction (Equation 4) is presented in U.S. Pat. No. 9,518,003, where hydroxy-ethyl-methyl carbonate is the product of reacting methanol with ethylene carbonate, where the ethylene carbonate is commercially produced by reacting ethylene oxide with carbon dioxide. The present invention combines the first two steps of chemical reaction depicted by (Equation 4), and hence bypasses the cost and energy intensive commercial process of ethylene carbonate.

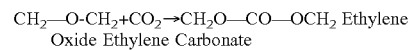
CH$_2$—O-CH$_2$+CO$_2$→CH$_2$O—CO—OCH$_2$ Ethylene Oxide Ethylene Carbonate

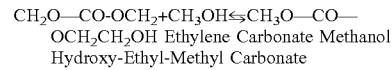
CH$_2$O—CO-OCH$_2$+CH$_3$OH⇌CH$_3$O—CO—OCH$_2$CH$_2$OH Ethylene Carbonate Methanol Hydroxy-Ethyl-Methyl Carbonate

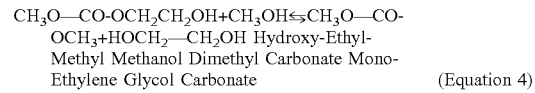
CH$_3$O—CO-OCH$_2$CH$_2$OH+CH$_3$OH⇌CH$_3$O—CO-OCH$_3$+HOCH$_2$—CH$_2$OH Hydroxy-Ethyl-Methyl Methanol Dimethyl Carbonate Mono-Ethylene Glycol Carbonate     (Equation 4)

DMC is further reacted to form methyl-ethyl carbonate by partial transesterification with ethanol (Equation 5) releasing one molecule of methanol that can be recycled. Complete transesterification with ethanol yields diethyl carbonate (Equation 6) releasing two molecules of methanol that can be recycled. These two forms of dialkyl carbonates have broad applications, including as electrolyte in lithium-ion batteries.

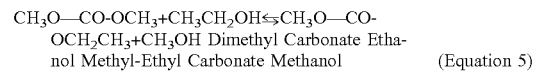
CH$_3$O—CO-OCH$_3$+CH$_3$CH$_2$OH⇌CH$_3$O—CO-OCH$_2$CH$_3$+CH$_3$OH Dimethyl Carbonate Ethanol Methyl-Ethyl Carbonate Methanol     (Equation 5)

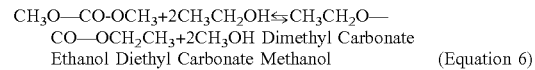
CH$_3$O—CO-OCH$_3$+2CH$_3$CH$_2$OH⇌CH$_3$CH$_2$O—CO—OCH$_2$CH$_3$+2CH$_3$OH Dimethyl Carbonate Ethanol Diethyl Carbonate Methanol     (Equation 6)

These and other objects and advantages of the present invention will be fully understood when taken in view of the Patent Drawings and Detailed Description of the Preferred Embodiment(s).

DESCRIPTION OF THE PREFERRED EMBODIMENTS

Referring to FIGS. 1-4, a process and system for producing purified concentrated dimethyl carbonate uses carbon dioxide as a feedstock, where the carbon dioxide is either captured from primary sources using a reactor, which may be a membrane reactor, a catalytic reactor, or an integrated adsorbent-catalytic reactor. The catalytic reactor may be employed which uses the concentrated carbon dioxide captured from primary sources by one of the commercial processes, such as, for example, the Amine absorption process.

As shown in FIGS. 1-4, the subject system 10 includes a distillation sub-system which is built with a Reaction Distillation Column 100, a Recycle column 200, and a Product Recovery column 300 interconnected one with another in a specific order. The Reaction Distillation Column (also referred to herein as a Reaction column or a Distillation column) 100 operates in conjunction with one or numerous side reactor(s) 42,72,114 and one or numerous separation units, such as for example, Permeation-Vaporization (PerVap) membrane(s). One or several PerVap membrane(s) may be integrated with either a membrane reactor 16 or a catalytic reactor, or, alternatively, with an integrated adsorbent-catalytic reactor, for selective separation of methanol as the permeate stream and the direct conversion by reaction of carbon dioxide with ethylene oxide and methanol in the presence of combined heterogeneous and homogeneous catalysts.

Interfacing the side reactors 42, 72, 114 with the reaction distillation column 100 without adverse impacts on the column performance requires careful design. The care is taken in the subject system on several criteria in the design interface which may include: 1) vapor flow should not be disturbed; 2) total or partial liquid flow to the side reactor using flow control valves should be employed; 3) liquid should be returned to the next stage, preferably to a tray or packed column embedded therein; 4) heat is preferably recovered using a feed/effluent heat exchanger for the side reactor, and the columns 100, 200, 300 should operate at different temperatures and pressures; and 5) interfacing design is based on commercially available hardware devices for minimizing operational risks.

Figure 1:
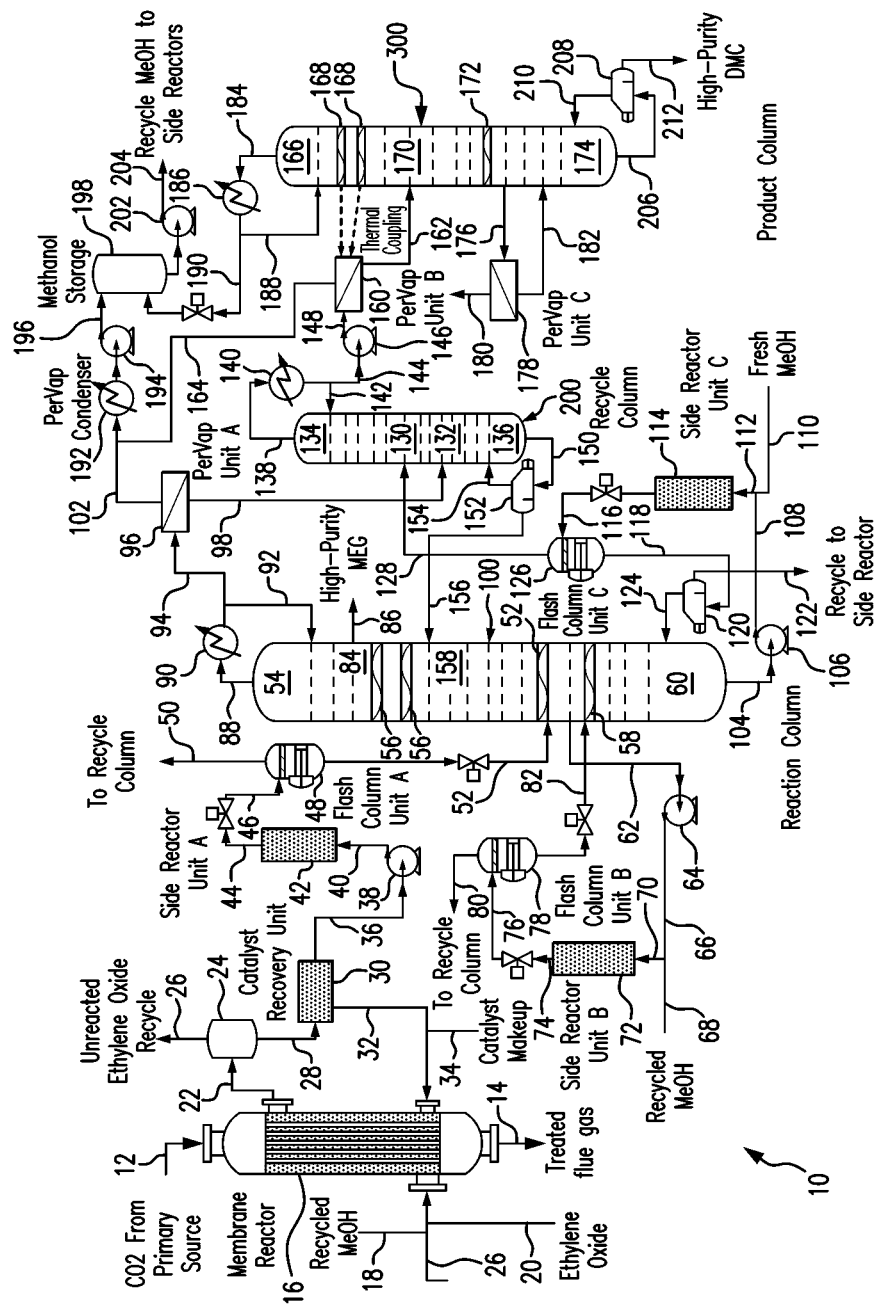
FIG. 1 is a schematic flow diagram of the membrane-assisted alkyl-carbonate process for carbon dioxide from primary sources of utility and industry processes.

Referring to FIG. 1, the Reaction Distillation Column 100 includes a plurality of recycling components and stages which produce a purified and concentrated dimethyl carbonate which exits as a product from a the final column i.e., the Product Recovery Column (also referred to herein as a Product Column or product Distillation Column) 300 on a dimethyl carbonate product line 212.

The system 10, as shown in FIG. 1, is designed for synthesis of alkyl carbonates using carbon dioxide recovered from primary source stream 12 gases using a membrane reactor system 16 and reacting with methanol 26 and ethylene oxide 20 to form hydroxy-ethyl-methyl carbonate 22, which is an intermediate substance for synthesis of dimethyl carbonate. The carbon dioxide lean treated flue-gas stream 14 exits from the Membrane Reactor 16.

As shown in FIG. 1, the recycled methanol (MeOH) is fed to the Membrane Reactor 16 on the recycled methanol stream 18.

Fresh ethylene oxide is fed to the Membrane Reactor 16 on the feed line 20. Recycled methanol from the line 204 is fed on the recycled methanol line 18 mixed with ethylene oxide line 20 along with the recycled unreacted ethylene oxide line 26. The mixed stream of stream 18 stream 20 and stream 26 can be in liquid or vapor phase before inserting into the Membrane Reactor 16.

Carbon dioxide 12 permeating though the membrane reacts with methanol and ethylene oxide inserted by streams 18 and 20 which are in liquid or vapor phases. Homogeneous catalyst recovered from catalyst recovery unit 30 is fed into the Membrane Reactor 16 on the line 32 along with make-up catalyst on the line 34. The resulting hydroxy-ethyl-methyl carbonate, as well dimethyl carbonate and unreacted ethylene oxide and methanol along with homogeneous catalyst, exit the Membrane Reactor 16 on the stream line 22 feeding into a flash tank 24 for separation of vapor and liquid phases. The recovered unreacted ethylene oxide is recycled into the Membrane Reactor 16 via the stream line 26.

The liquid stream 28 from the flash tank 24 is fed into the Catalyst Recovery unit 30. Recovered homogeneous catalyst dissolved in methanol is fed back to the Membrane Reactor 16 on the line 32. The product stream from the catalyst recovery unit 30 is fed to the first side reactor unit A 42 on the line 36 by the pump 38 feeding the side reactor unit A 42 via line 40.

The side reactor unit A 42 shown in FIGS. 1-4, is packed with a heterogeneous catalyst in order to facilitate the reaction of hydroxy-ethyl-methyl carbonate with methanol for synthesis of dimethyl carbonate and mono ethylene glycol.

The product stream exiting the side reactor unit A 42 on line 44 is reduced in pressure by a valve on line 46 to produce a vapor, a liquid or a vapor/liquid mixture. The product stream on the line 46 is fed into the flash column unit A 48. The unit 48 includes a structured packing on the top and an internal heat exchanger for vaporization. The vapor product on the line 50 consists of the high concentration dimethyl carbonate or azeotropic mixture of dimethyl carbonate and methanol.

The product stream on the line 50 is fed into the Recycle Column 200 for further concentration of dimethyl carbonate and recovery and recycling of unreacted hydroxy-ethyl-methyl carbonate.

The liquid product stream 52 from the Flash Column unit 48 consisting of the unreacted hydroxy-ethyl-methyl carbonate and methanol along with dimethyl carbonate and mono ethylene glycol is fed to the first distillation column 100. The hydroxy-ethyl-methyl carbonate is converted to dimethyl carbonate and mono ethylene glycol by way of the multiple side reactors 72 and 114.

It is to be understood that a number of the side reactors may vary and more or less of the side reactors than that shown in the present embodiment may be used, including the side reactor 72 connected to the bottom of the Reaction Distillation Column 100. As an example only and for the simplicity and in sake of brevity and clarification of the description, a flow process for one of the many of the contemplated side reactors will be presented in the following paragraphs.

With respect to the process associated with the side reactor Unit B 72, a product stream is side drawn from one of the stages of the Reaction Distillation Column 100 which flows through the product line 62 to a pump 64 which inserts the product stream into the side reactor Unit B 72 along with the recycle methanol stream 68 and the recycle stream 122 from the bottom of the Column 100.

The hydroxy-ethyl-methyl carbonate is subsequently converted to dimethyl carbonate and mono ethylene glycol which exit the side reactor unit B 72 on the product line 74 and is fed into the flash column unit B 78 after reducing the pressure on line 76. The vapor product stream 80 consisting of concentrated dimethyl carbonate or azeotropic mixture of dimethyl carbonate and methanol is fed from the Flush Column Unit B 78 to the Recycle Volumn 200 for further concentration of dimethyl carbonate and recycling of the unreacted hydroxy-ethyl-methyl carbonate into the Reaction Distillation Column 100.

The liquid product stream consisting of the unreacted hydroxy-ethyl-methyl carbonate, mono-ethylene glycol, low-concentration dimethyl carbonate and unreacted methanol is fed back into the Reaction Distillation Column 100 on the line 82 on a stage lower than the side draw stage. It is to be understood that multiple side reactors may be used for achieving desired conversion of hydroxy-ethyl-methyl carbonate to dimethyl carbonate and mono ethylene glycol.

As depicted in FIG. 1, the product stream returning on the re-entry product lines 82 is inserted into the Reaction Distillation Column 100 one stage lower than the withdrawal stage represented by the product line 62. The distillation stages where the product streams are introduced into the Reaction Distillation Column 100 are equipped with thermal devices 58 to selectively vaporize dimethyl carbonate and mono ethylene glycol. The thermal devices 58 may be incorporated on distillation trays or within packed columns. Thermal devices 58 are thermally coupled with thermal devices 168 incorporated in the Product Distillation Column 300 or the overhead condenser 186 for recovering heat energy from the Product Distillation Column 300 operating at a higher temperature than the Reaction Distillation Column 100. Well-known heat transfer fluids or systems, such as, for example, a heat pipe, may be used to transfer the heat energy from Product Distillation Column 300 to the Reaction Distillation Column 100.

A product mixture consisting of the unreacted hydroxy-ethyl-methyl carbonate and methanol along with low concentration of dimethyl carbonate and mono ethylene glycol accumulates in the bottom portion 60 of the distillation column 100 and is fed to the side reactor unit C 114 via the stream line 104 and the pump 106 on line 108 along with fresh methanol feed on line 110 for further conversion of residual hydroxy-ethyl-methyl carbonate and the liquid product stream 118 from the flash column unit C 126 is returned to the heat exchanger 120, also referred to herein as a reboiler. Dimethyl carbonate, along with the unreacted methanol and mono ethylene glycol, is vaporized in through the reboiler 120. Vapor phase dimethyl carbonate, along with methanol and mono ethylene glycol in vapor phase, is re-introduced into the Reaction Distillation Column 100 via the streamline 124. The liquid product stream 122 containing a higher concentration of the unreacted hydroxy-ethyl-methyl carbonate from the reboiler 120 is fed to the side reactors for further conversion to dimethyl carbonate and mono ethylene glycol.

A product mixture consisting primarily of methanol, dimethyl carbonate and mono ethylene glycol flows upward in the Reaction Distillation Column 100. On stage 158 of the Reaction Distillation Column 100, the bottom product stream consisting of the unreacted hydroxy-ethyl-methyl carbonate 156 fed from the Recycle Column 200 is mixed with the product stream rising from the lower section of the Reaction Distillation Column 100. Thermal devices 56, such as internal cooler/reflux condenser, preferably condenses the unreacted hydroxy-ethyl-methyl carbonate, thus increasing the concentration of other products rising into the upper section 54 of the Reaction Distillation Column 100.

A high-purity mono ethylene glycol (MEG) is side drawn on the line 86 from the upper stage 84 of the Reaction Distillation Column 100. A product mixture stream 88 consisting primarily of methanol and dimethyl carbonate formed at the top portion 54 of the Distillation Column 100 is fed to the heat exchanger 90, also referred to herein as an overhead total condenser. The overhead product stream 94 is fed into the PerVap 96 for selective separation of fraction of methanol from product stream 94. A fraction of the condensate is returned, as a reflux, from the overhead total condenser 90 to the first stage of the Reaction Distillation Column 100 via the stream 92.

The permeate vapor stream 102 with nearly pure methanol from the PerVap membrane 96 is fed into heat exchanger 192, also referred to herein as a PerVap condenser. The retentate liquid stream 98 from the PerVap membrane 96 consisting of a higher concentrated dimethyl carbonate is fed into the Recycle Column 200 at its stage location 132.

The product streams 50, 80 and 128 in the vapor phase exiting from the flash columns 48, 78 and 126, respectively, that are attached to the side reactors 42, 72 and 114, respectively, are fed to the Recycle Column 200 at the stage 130 located above the stage 132.

As shown in FIG. 1, the product stream (containing the unreacted hydroxy-ethyl-methyl carbonate along with methanol) flows down to the bottom section 136 of the Recycle Column 200. The bottom product is fed via the line 150 from the bottom section 136 into a heat exchanger, also referred to herein as a reboiler, 152. The vapor product from the reboiler 152 is fed back into the Recycle Column 200 via the line 154. The liquid product from the reboiler 152 consisting of a higher concentration of unreacted hydro-ethyl-methyl carbonate is fed back into the Reaction Distillation Column 100, at the stage 158, via the line 156. The volatile product stream exits from the top section 134 of the Recycle Column 200 via the line 138 and flows into a heat exchanger 140, also referred to herein as an overhead condenser. Fraction of the condensate from the overhead condenser 140 is returned, as the reflux stream 142, to the first stage of the Recycle Column 200.

As shown in FIG. 1 the major fraction of the condensate from the overhead condenser 140 is pumped via the line 144 to a higher pressure by a pump 146 and is fed into the PerVap membrane Unit B 160 for selective separation of methanol to increase the concentration of dimethyl carbonate. The permeate vapor stream 164 is fed into the PerVap condenser 192. The liquid retentate stream 162 is fed into the stage 170 of the Product Column 300.

The Product Column 300 operates at a higher pressure for effective separation of azeotropic mixture of dimethyl carbonate and methanol into pure overhead and bottom products. In order to enhance the separation, a single PerVap membrane unit C 178, or multiple side PerVap units, are interlinked with the Product Column 300. A side draw stream 176 is fed into the PerVap membrane unit C 178. A nearly pure permeate vapor stream 180 is fed into the PerVap condenser 192.

The dimethyl carbonate concentrated retentate stream 182 is returned to the Product Column 300 at a stage located lower than the side drawn stage. An internal heat transfer device 172 is incorporated in the Production Column 300 to further enhance the separation by vaporizing methanol that flows upward to the top section 166 of the Production Column 300. The methanol-rich stream flows to the top section 166 of the Production Column 300 and encounters heat transfer devices 168, also referred to herein as internal coolers or reflux condensers, to condense out dimethyl carbonate, thus increasing methanol concentration in the vapor phase.

The heat extracted by the internal coolers or reflux condensers 168 is utilized by one or more PerVap membrane units 160. The heat extracted by the internal coolers or reflux condensers 168 is also utilized within the Reaction Distillation Column 100. Incorporating the side connect PerVap membrane(s) and the internal heat transfer devices in the subject system 10 enhances the energy efficiency of the Product Column 300 and the product recovery.

The methanol rich product stream exiting the top section 166 of the Product Column 300 is fed into the heat exchanger 186, also referred to herein as an overhead condenser. A fraction of the condensate from the heat exchanger 186 is returned, as a reflux, on the line 188 to the first stage of the Production Column 300.

The major fraction of the condensate stream 190 is fed into the methanol storage tank 198. The permeate vapor streams 102, 164, and 180 from all PerVap membranes units A, B and C 96, 160 and 178, respectively, are condensed by the heat exchanger 192, also referred to herein as a PerVap condenser, and the condensate of fed into the methanol storage tank 198 by the pump 194 via the line 196. The methanol from the storage tank 198 is pumped by the pump 202 via the line 204 to the side reactors and the membrane reactor.

As shown in FIG. 1, the product stream 206 with high-concentration of dimethyl carbonate is withdrawn from the bottom portion 174 of the Product Distillation Column 300 and is fed into the heat exchanger 208, also referred to herein as a reboiler, for vaporizing a small fraction of methanol that may have been carried down the Product Distillation column 300 and fed back on line 210 into the Product Distillation Column 300. The purified high-concentration dimethyl carbonate is withdrawn via the line 212 as a final product.

Figure 2:
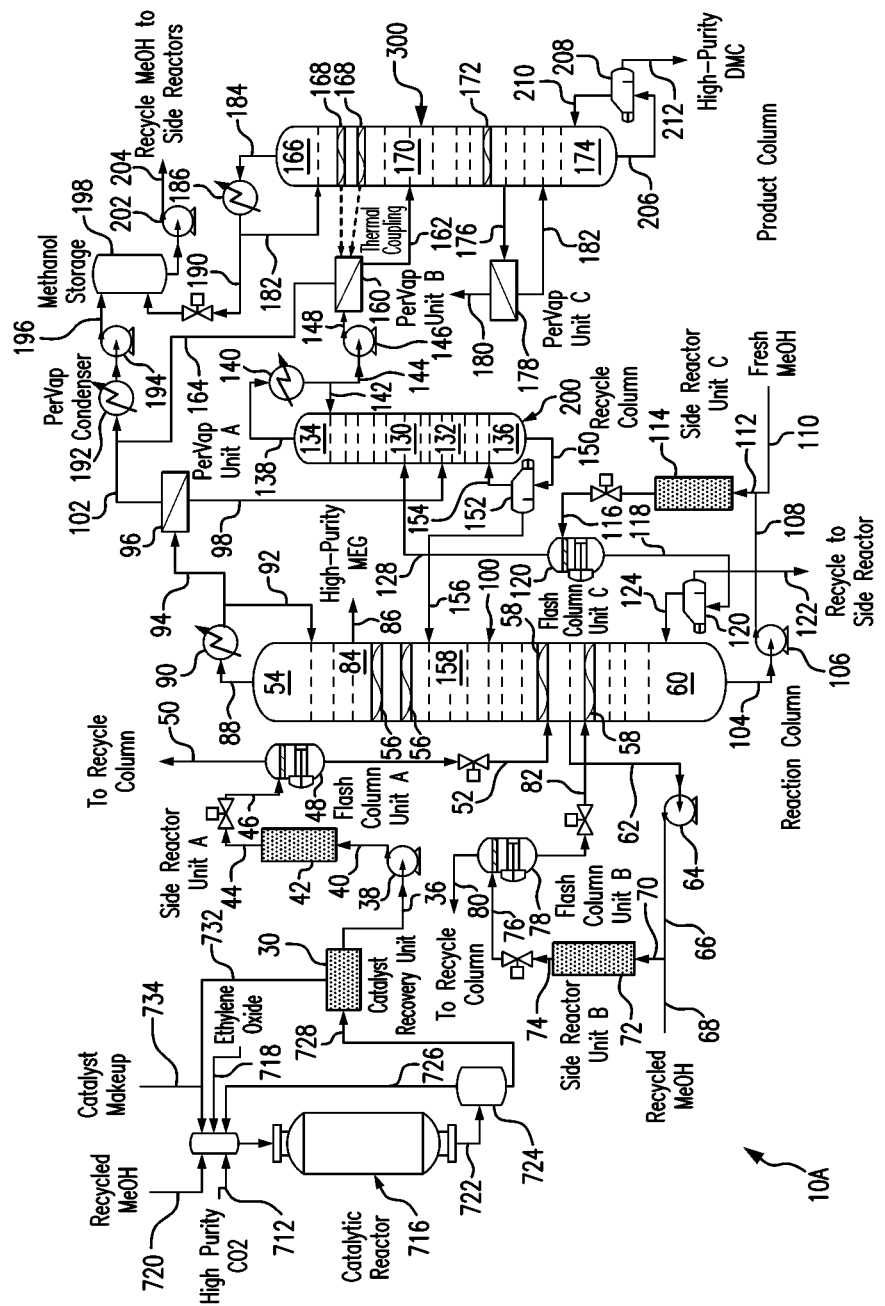
FIG. 2 is a schematic flow diagram of the catalytic direct conversion process for high-purity carbon dioxide captured from primary sources.

Referring to FIG. 2, in an alternative implementation 10A of the subject system, the membrane reactor 16 and associated components (shown in FIG. 1) are replaced by a Catalytic Reactor 716 and corresponding components for conversion of high-purity carbon dioxide captured by one of the commercial or emerging carbon capture technologies.

Specifically, in the embodiment of the subject system 10A depicted in FIG. 2, high-purity carbon dioxide 712 is fed at the top of the Catalytic Reactor 716. A combined stream of the high-purity carbon dioxide stream 712, recycled methanol stream 720, ethylene oxide stream 718, recycled unreacted vapor phase carbon dioxide and ethylene oxide from the flash tank 724, recycled catalyst stream 732 and the makeup catalyst dissolved in methanol stream 734 are also fed at the top of the Catalytic Reactor 716 for a down-flow catalytic reactor in a trickle-bed reactor mode. The combined feed stream entering the Catalytic Reactor 716 consists of a vapor phase and a liquid phase.

The product stream 722 containing hydroxy-ethyl-methyl carbonate along with the unreacted methanol, ethylene oxide, carbon dioxide, and homogeneous catalyst is fed to the flash tank 724 The vapor stream 726 from the flash tank 724 consisting of the unreacted ethylene oxide and carbon dioxide is recycled back into the Catalytic Reactor 716. The liquid stream 728 is fed to the Catalyst Recovery unit 30. The subsequent process is identical to that shown in FIG. 1.

Figure 3:
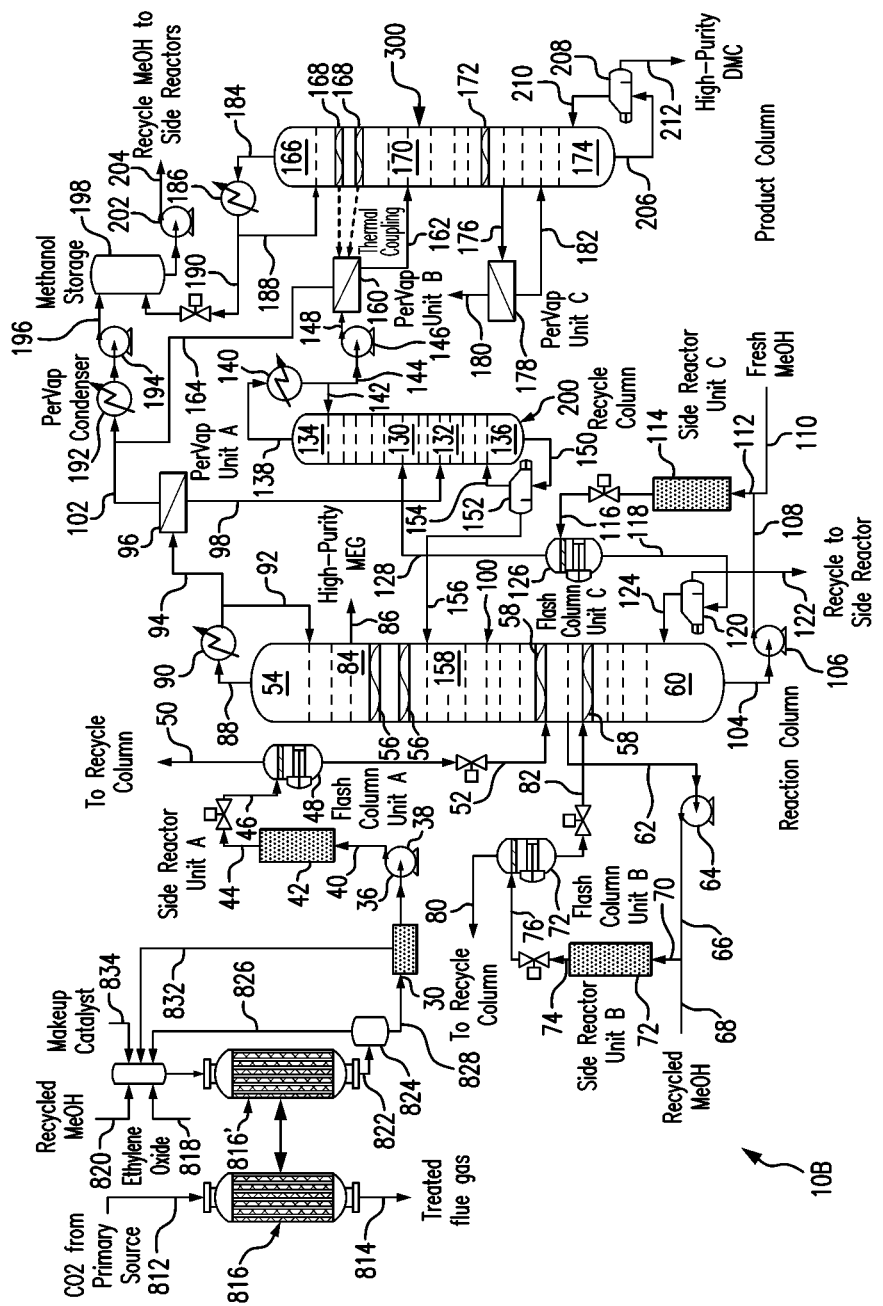
FIG. 3 is a schematic flow diagram of the adsorbent-catalytic reactor based alkyl-carbonate process for carbon dioxide from primary sources of utility and industry processes.

Referring to FIG. 3, in another alternative embodiment 10B of the subject system, the membrane reactor 16 and associated components shown in FIG. 1 are replaced by adsorbent-catalytic reactors 816 and 816' for capture and conversion of carbon dioxide from primary sources. Two or more adsorbent-catalytic reactors may be used for alternate processes of capturing carbon dioxide from a primary source and converting to hydroxy-ethyl-methyl carbonate. A primary source of carbon dioxide on the line 812 is fed into the adsorbent-catalytic reactor 816 to adsorb carbon dioxide using commercial adsorbents or new solid adsorbents.

When the adsorbent—catalytic reactor 816 is nearly saturated with carbon dioxide, the primary source stream 812 is switched to another reactor unit 816' that has been cleared of carbon dioxide by reaction with ethylene oxide and methanol. The reactor 816 is thus switched to the alternating reaction mode as depicted by 816'.

The carbon dioxide lean treated flue-gas stream 814 exits from the reactor 816.

The combined stream of a recycled ethylene oxide stream 826, recycled methanol stream 820, fresh feed ethylene oxide stream 818, recycled catalyst stream 832, and the make-up catalyst dissolved in methanol stream 834 are also fed at the top for a down-flow catalytic reactor, also referred to herein as a trickle-bed reactor. The combined feed stream entering the Catalytic Reactor 816 can be liquid, vapor, or vapor and liquid mixed.

The product stream 822 containing hydroxy-ethyl-methyl carbonate along with unreacted methanol, ethylene oxide, and homogeneous catalyst is fed to the flash tank 824. The vapor stream 826 from the flash tank 824 consisting of unreacted ethylene oxide is recycled back into the adsorbent-catalytic reactor 816. The liquid stream 828 is fed to the catalyst recovery unit 30. The subsequent process is identical to that shown in FIG. 1.

Figure 4:
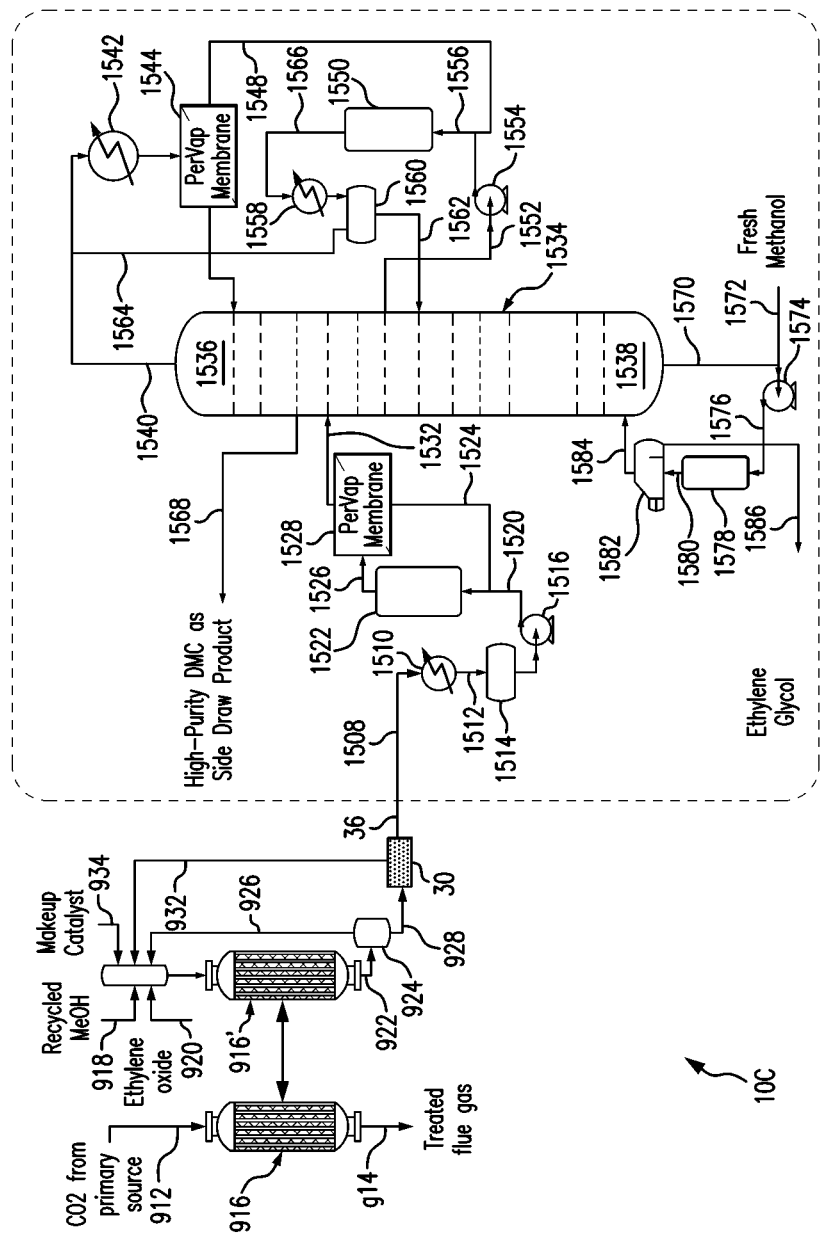
FIG. 4 is a schematic flow diagram of the adsorbent-reactor integrated with the alkyl-carbonate process for the single column of the prior art.

FIG. 4 depicts another alternative embodiment 10C of the subject system, where the ethylene carbonate process presented in U.S. Pat. No. 9,518,003 is replaced by the adsorbent-catalytic reactors 916, 916' for a direct conversion of carbon dioxide from primary sources. The adsorbent-catalytic reactor 916 and 916' are identical to the reactors 816 and 816' presented in FIG. 3.

Two or more adsorbent-catalytic reactors 916, 916' may be used for alternate processes of capturing carbon dioxide from a primary source and converting to hydroxy-ethyl-methyl carbonate. A primary source of carbon dioxide on the line 912 is fed into the adsorbent-catalytic reactor 916 to adsorb carbon dioxide using commercial adsorbents or new solid adsorbents.

When the adsorbent-catalytic reactor 916 is nearly saturated with carbon dioxide, the primary source stream 912 is switched to another reactor unit 916' that has been cleared of carbon dioxide by reaction with ethylene oxide and methanol. The reactor 916 is thus switched to the alternating reaction mode as depicted by 916'.

The carbon dioxide lean treated flue-gas stream 914 exits from the reactor 916.

The combined stream of a recycled ethylene oxide stream 926, recycled methanol stream 920, fresh feed ethylene oxide stream 918, recycled catalyst stream 932, and the make-up catalyst dissolved in methanol stream 934 are also fed at the top for a down-flow catalytic reactor, also referred to herein as a trickle-bed reactor. The combined feed stream entering the Catalytic Reactor 916 can be liquid, vapor, or vapor and liquid mixed.

The product stream 922 containing hydroxy-ethyl-methyl carbonate along with unreacted methanol, ethylene oxide, and homogeneous catalyst is fed to the flash tank 924. The vapor stream 926 from the flash tank 924 consisting of unreacted ethylene oxide is recycled back into the adsorbent-catalytic reactor 916. The liquid stream 928 is fed to the catalyst recovery unit 30.

The membrane reactor 16 depicted in FIG. 1 or the catalytic reactor 716 depicted in FIG. 2 can also be used in the embodiment of FIG. 4.

The remaining part of the process is identical to that presented in U.S. Pat. No. 9,518,003 with the stream and components numbers identified by pre-text of 1, such as, for example, the column 534 (in '003 Patent) is identified as 1534 (in FIG. 4 herein).

Figure 5:
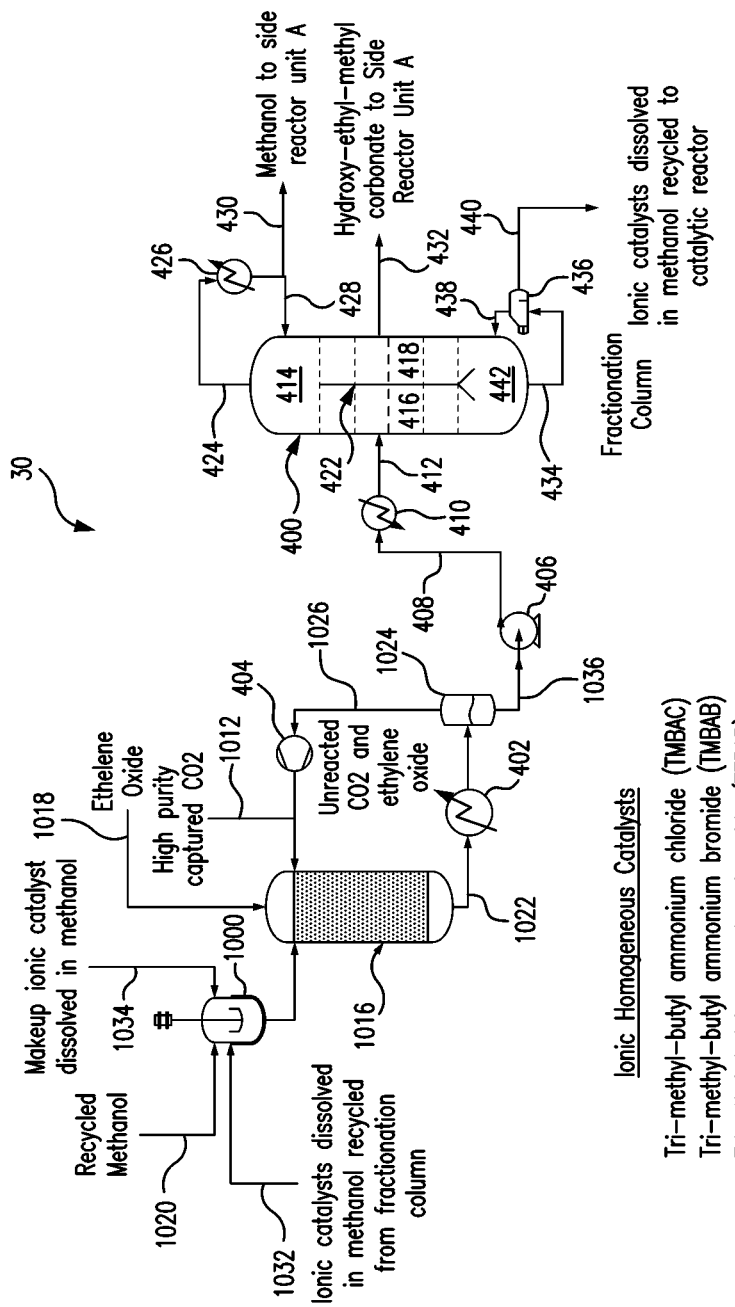
FIG. 5 is a schematic drawing of catalyst recovery and recycling back into the membrane reactor, catalytic reactor and adsorbent-catalytic reactor.

FIG. 5 depicts a schematic flow diagram of the catalyst recovery unit 30 referenced in FIGS. 1, 2, 3 and 4. As an example, the catalyst recovery unit 30 is connected to a direct-conversion catalyst reactor 1016.

The recycled methanol 1034 is fed into the catalyst chamber 1000, and the makeup ionic catalyst 1034 is fed into the catalyst chamber 1000 to be dissolved in methanol. In addition, the ionic catalysts 1032 dissolved in methanol are fed in the catalyst chamber 1000 from the fractionation column 400. Thus prepared catalysts are fed form the catalyst chamber 1000 into the catalyst reactor 1016.

Ethelene oxide 1018 and high purity captured $CO_2$ 1012 are fed into the catalytic reactor 1016.

The product stream 1022 exiting the catalytic reactor 1016 is cooled down by the heat exchanger 402 to enhance the effective separation of vapor phase 1024 containing unreacted ethylene oxide and carbon dioxide that are recycled via the stream 1026. The liquid stream 1036 consisting of hydroxy-ethyl-methyl carbonate, unreacted methanol, homogeneous catalyst and traces of dimethyl carbonate and mono-ethylene glycol is fed into the heat exchanger 410, also referred to herein as a side reboiler, for generating vapor-liquid stream 412.

The stream 412 is introduced into the fractionation column 400, also referred to herein as a divided-wall column equipped with the partition 422 to divide the column into two sections 416 and 418. A lighter fraction, mainly methanol with traces of dimethyl carbonate and mono-ethylene glycol, flows upward to upper section 414, while the heavier fraction, mainly, hydroxy-ethyl-methyl carbonate and homogeneous catalyst, flow downward towards the lower section 442.

The vapor stream 424 exiting from the upper section 414 is condensed by the heat exchanger 426, also referred to herein as an overhead condenser. A fraction of the condensate is returned to the first stage of the fractionation column 400. The overhead product stream 430 is combined with hydroxy-ethyl-methyl stream drawn via the line 432 from the middle section 418 of the fractionation column 400 and is fed to the Side Reactor Unit A 42 depicted in FIG. 2.

A homogeneous stream 434 consisting of hydroxy-ethyl-methyl carbonate is withdrawn from the bottom section 442 and fed into heat exchanger 436, also referred to herein as a reboiler. The vapor stream 438 from the reboiler 436 is retuned below the last stage of the fractionation column 400.

The liquid stream 440 with a concentrated homogeneous catalyst is recycled to the catalyst reactor 1016 via the stream 1032. The vapor with a higher concentration of hydroxy-ethyl-methyl carbonate from the lower section 442 of the fractionation Column 400 is divided by the dynamic divider at the bottom of the dividing wall 422. The rising vapor stream with a higher concentration combined with a reflux returning from the upper section 414 of the section 418 effectively concentrate hydro-ethyl-methyl carbonate and is withdrawn at an appropriate state via the stream 432. The divided-wall fraction column 400 is ideally suited for concentrating three products with varying volatility, such a volatile methanol, intermediate hydroxy-ethyl-methyl carbonate, and homogeneous catalyst with low volatility. The catalyst recovery unit 30 presented in FIG. 5 may be employed with any of the direction conversion reactors presented in FIGS. 1, 2 and 3.

Figure 6:
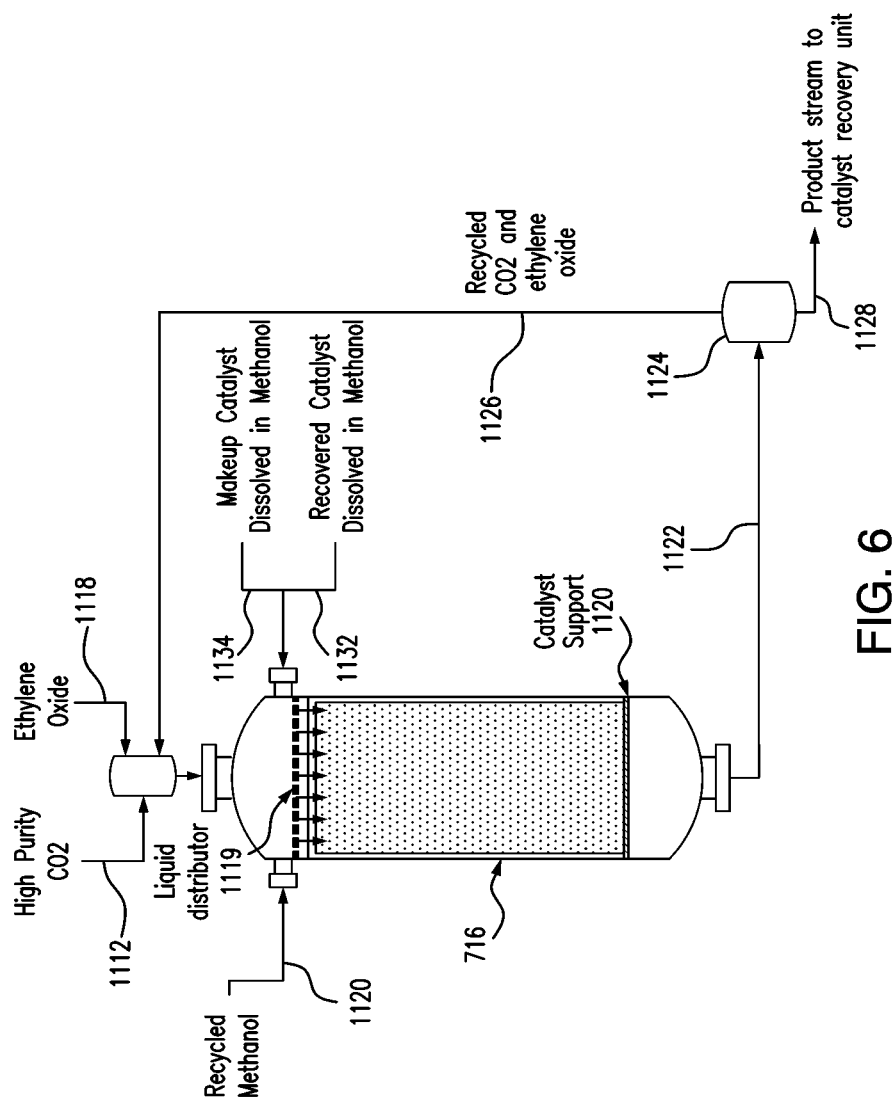
FIG. 6 is a schematic diagram of the catalytic reactor.

FIG. 6 depicts a schematic flow diagram representing catalytic reactor 716 used in FIG. 2. Transesterification heterogeneous catalyst, such as Amberlyst A-26, is packed within the reactor 716 and is supported by a sieve tray 1120. The combined gaseous phase stream consisting of high-purity carbon dioxide stream 1112, ethylene oxide stream 1118 and are recycled unreacted ethylene oxide and carbon dioxide stream 1126 are mixed in manifold.

The mixed vapor stream is fed from the top of the reactor 716. The liquid streams which consist of the recycled methanol stream 1120 and a combined stream of 1126 and 1128 (consisting of homogeneous catalysts 1132 recovered from the catalyst recovery unit 30 and a fresh makeup homogeneous catalyst 1134 dissolved in methanol) are fed at the top section of the reactor 716.

The liquid is uniformly distributed across the top of the packed-bed catalyst using a commercial liquid distributor 1119. The vapor and liquid flow down in a trickle-bed reactor mode of operation. The product stream exits the reactor 716 via the stream 1122 and is fed into the flash tank 1124 as depicted in FIG. 2. The subsequent process is identical to that presented in FIG. 2.

Figure 7:
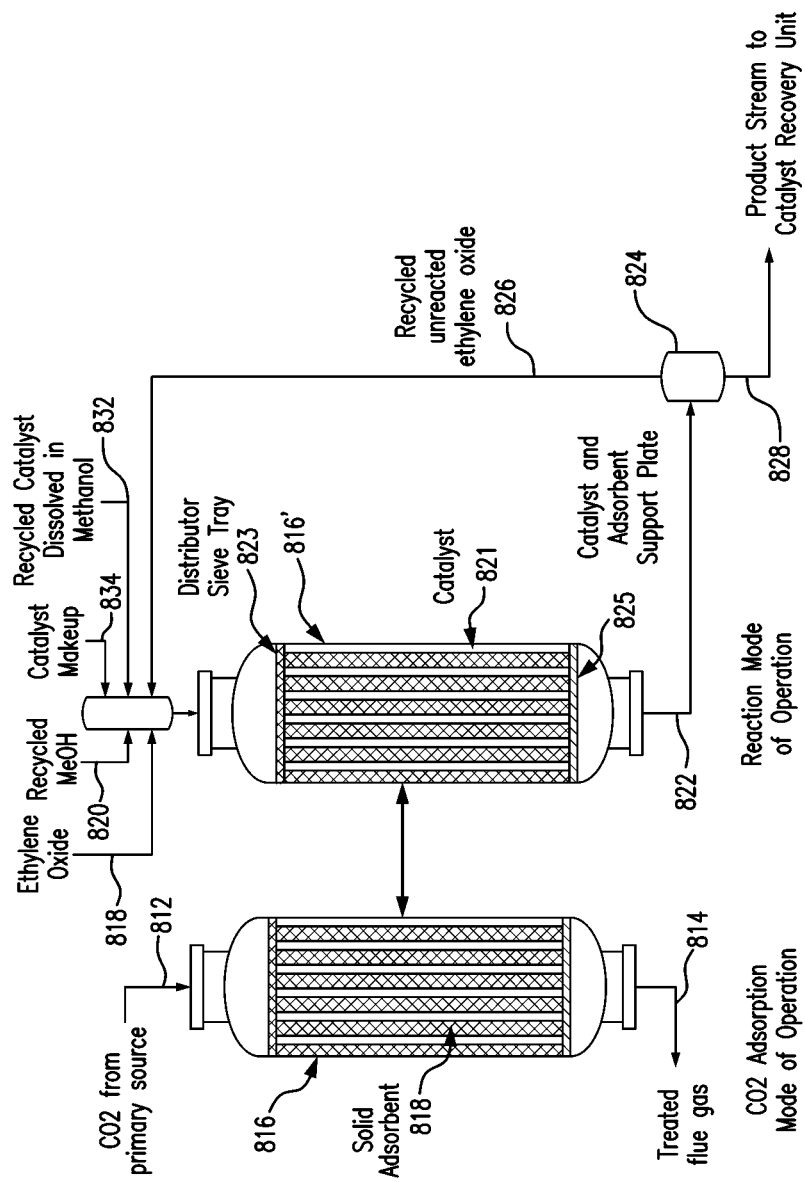
FIG. 7 is a schematic of adsorbent-catalytic reactor.

FIG. 7 is illustrative of a schematic flow diagram representing adsorbent-catalytic reactor 816 depicted in FIG. 3. Transesterification heterogeneous catalyst 821, such as Amberlyst A-26, is packed within the reactor 816 and 816' along with a commercial or one of the new solid adsorbents, such as metal-organic framework (MOF) or nanowire or nanoparticle or an alternate solid adsorbent 818 and supported by the sieve tray 823 and the support plate 825. Two or multiple adsorbent-catalytic reactors 816, 816' may be used for the alternate processes of capturing carbon dioxide from a primary source and converting to hydroxy-ethyl-methyl carbonate. Primary source of carbon dioxide on line 812 is fed into the reactor 816 for adsorption using commercial or new solid adsorbents. The saturation of the reactor 816 with the adsorbed carbon dioxide is continuously monitored by detecting carbon dioxide in the stream 814. When the reactor 816 is nearly saturated with the carbon dioxide primary source, the stream 812 is switched to another reactor unit 816' that has been cleared of carbon dioxide by reaction with ethylene oxide and methanol. The reactor 816 thus is switched to reaction mode as depicted by 816'.

The combined stream of recycled ethylene oxide stream 826, recycled methanol stream 820, fresh feed ethylene oxide stream 818, recycled catalyst stream 832 and make-up catalyst dissolved in methanol stream 834 are also fed from at top for a down flow catalytic reactor in a trickle-bed reactor mode of operation by the uniform distribution of the vapor and liquid phase by the distribution tray 823.

The reaction mode of operation of 816' is continued until adsorbed carbon dioxide is consumed as indicated by sensor located on the outlet stream 822 or inside the reactor. The product stream 822 containing hydroxy-ethyl-methyl carbonate along with the unreacted methanol, ethylene oxide, and homogeneous catalyst is fed to the flash tank 824. The subsequent process is identical to FIG. 3.

Figure 8:
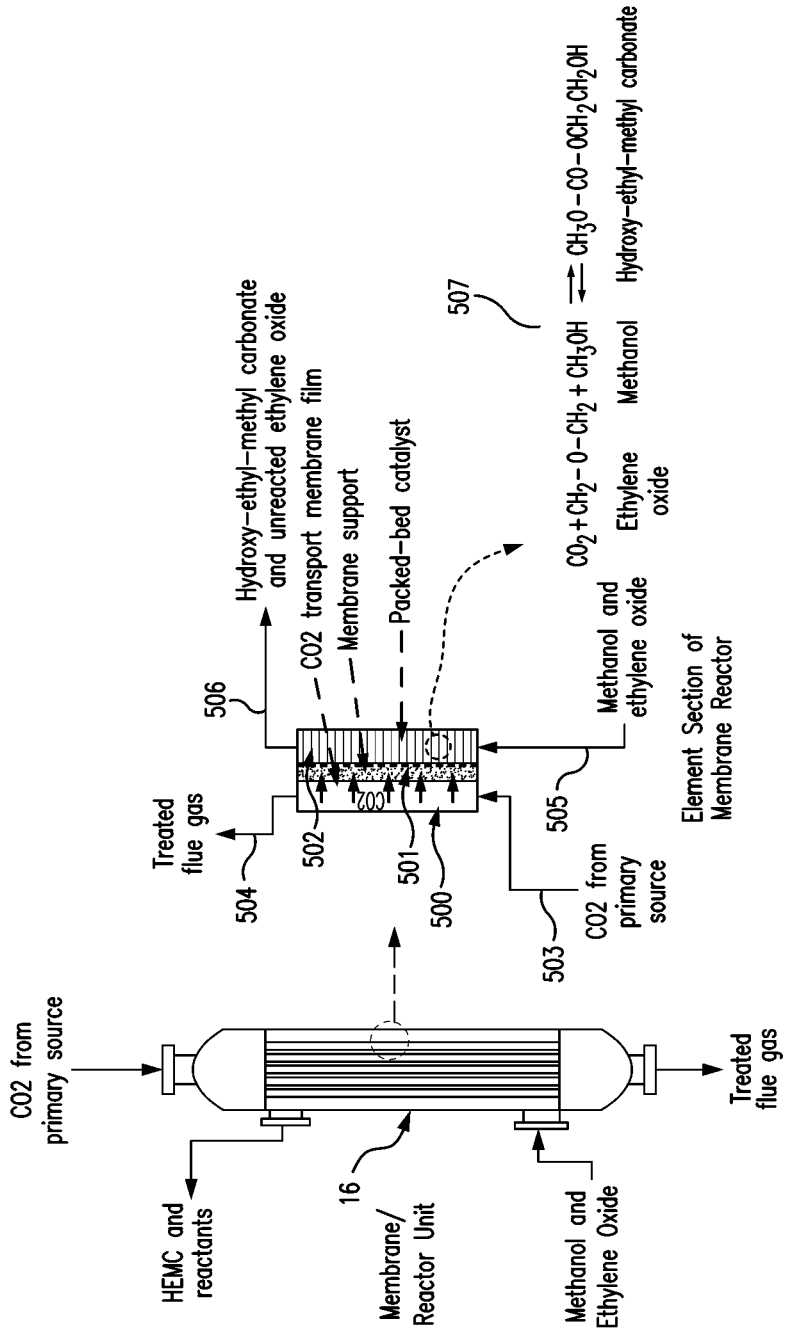
FIG. 8 is a membrane element with catalyst packed in the reactant flow channel of the membrane reactor.
Figure 9:
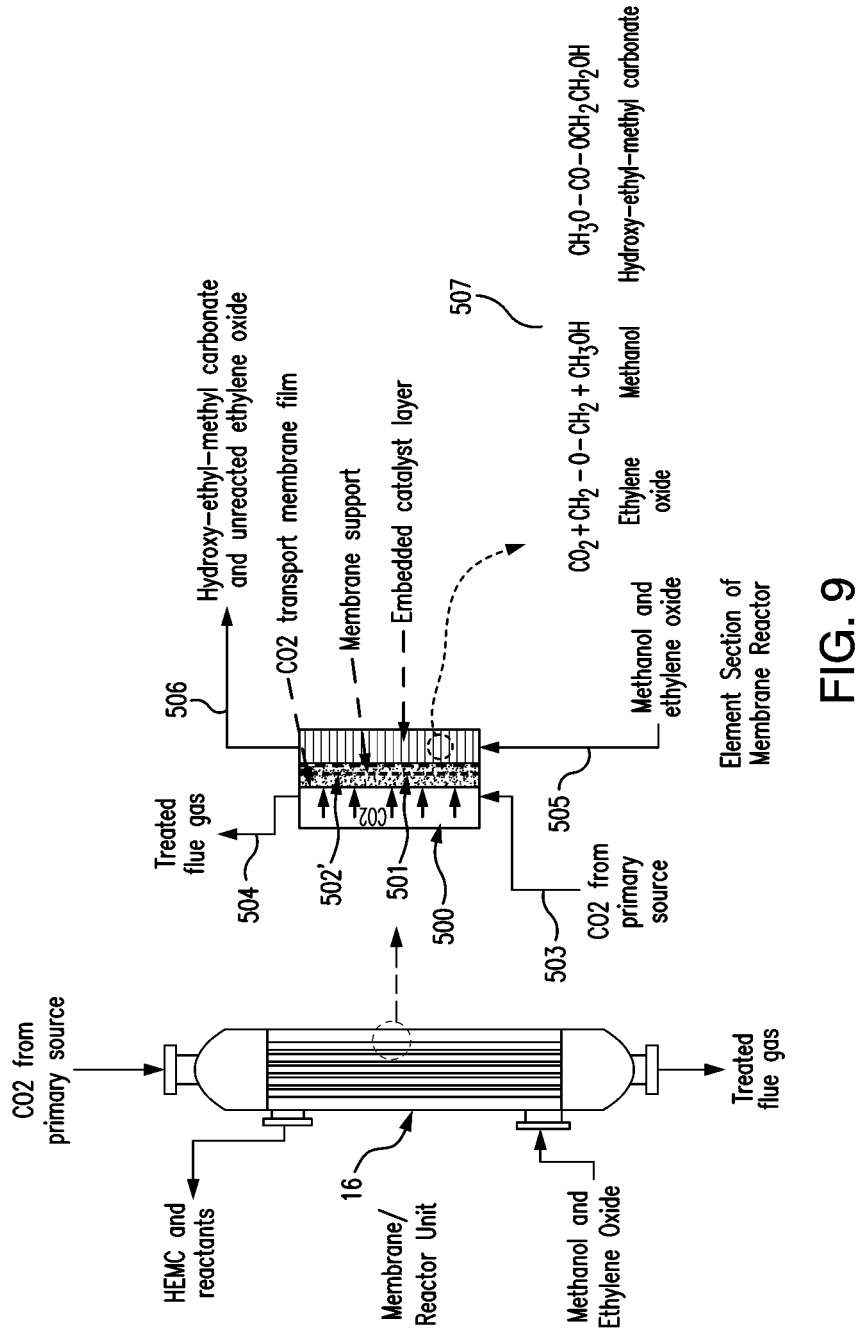
FIG. 9 is a membrane element with catalyst embedded on the membrane surface on the side of the reactant flow channel in the membrane reactor.

FIGS. 8 and 9 depict two alternative design concepts of the membrane reactor 16 presented in FIG. 1. Specifically, FIGS. 8 and 9 represent an element section 500 of the membrane reactor 16 where the membrane 501 includes a membrane support and carbon dioxide transport membrane film. In FIG. 8, catalysts 502 are packed on the other side of the membrane in the form of a packed-bed catalyst, while in FIG. 9, the catalyst 502' is embedded on the membrane surface. In FIG. 8, the reactants (ammonia and methanol) flow 505 passes through the catalysts.

The carbon dioxide stream 503 from primary sources flows through one side of the membrane 501 and, as the carbon dioxide diffuses through the membrane, the carbon dioxide reacts with methanol and ethylene oxide in the presence of heterogeneous and homogeneous catalysts in the bulk flow region as depicted by the reaction equation 507. The resulting product exits via the streamline 506. The carbon dioxide lean treated flue-gas 504 exits form the membrane reactor 16.

In FIG. 9, the carbon dioxide diffuses through the membrane and reacts with methanol and ethylene oxide at the membrane surface on which catalysts 502' are embedded. The product methyl carbamate is then carried away by flowing methanol and exit via the streamline 506.

Figure 10:
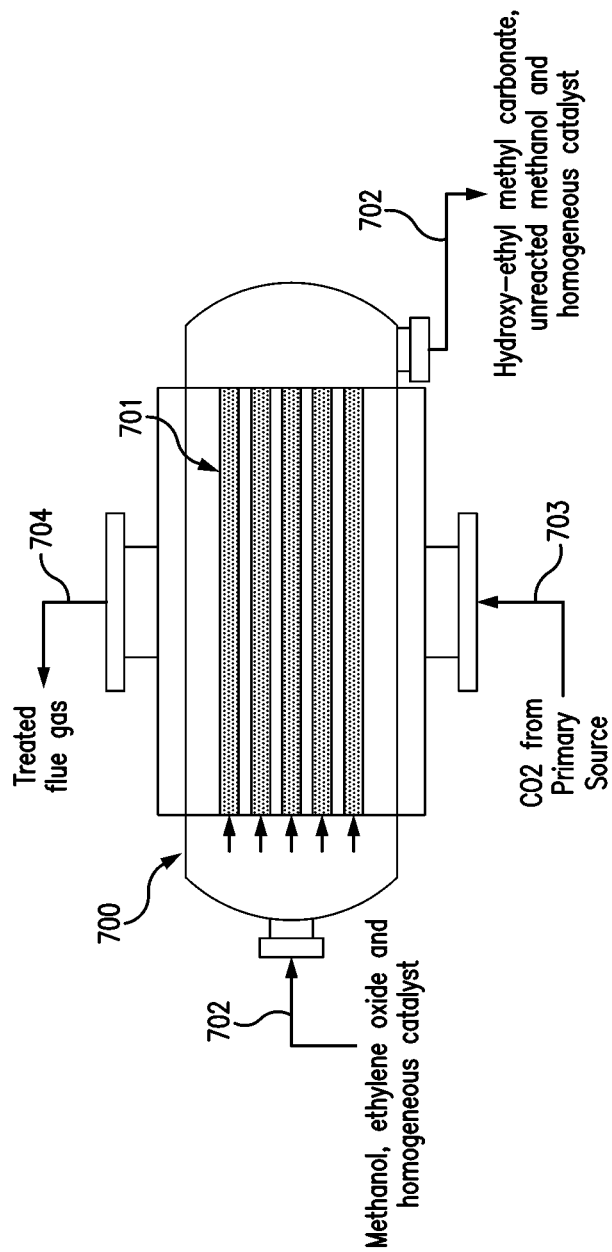
FIG. 10 is a schematic drawing of the membrane reactor with shell-and-tube module with cross-flow configuration.
Figure 11:
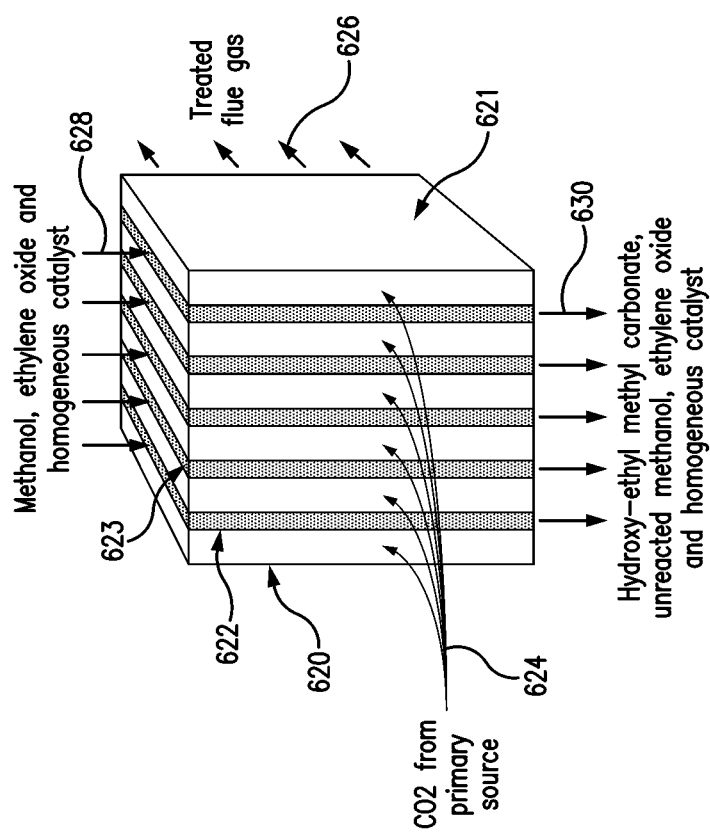
FIG. 11 is a schematic drawing of the membrane reactor with cross-flow parallel-plate module.
Figure 12:
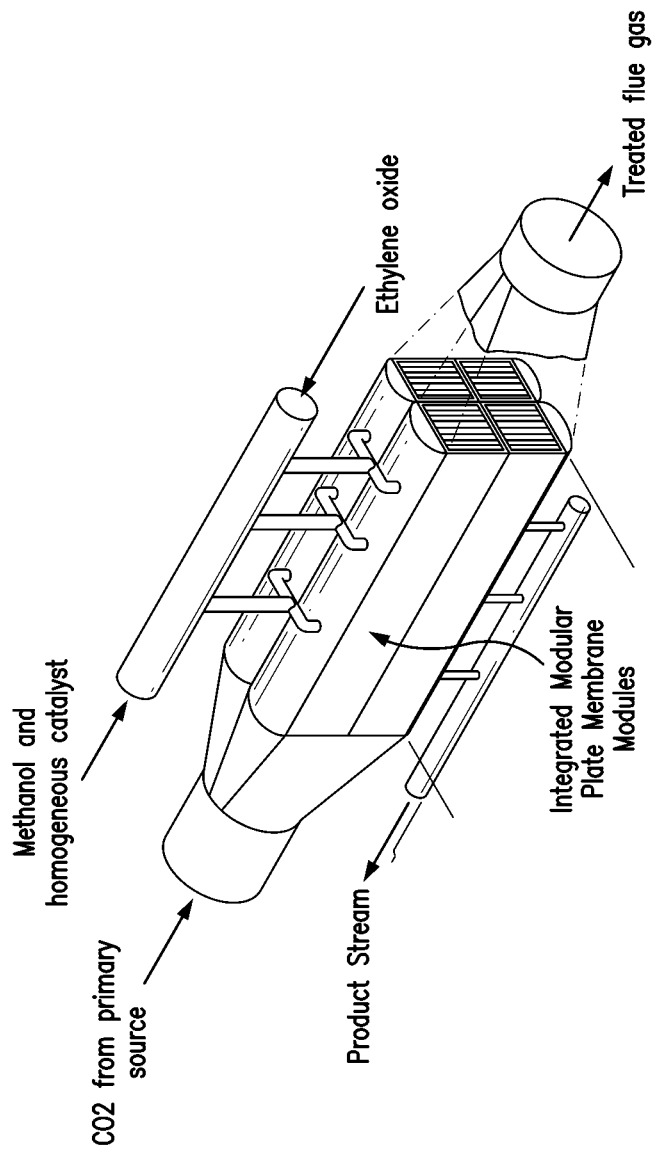
FIG. 12 is a schematic design of a parallel-plate membrane module.

FIGS. 10, 11 and 12 depict three alternative configurations of the membrane modules. FIG. 10 represents a shell-and-tube module 700 with tubular membranes 701 providing a cross-flow of the carbon dioxide stream 703. The tubular membrane 701 may have carbon dioxide transport membrane film either inside or outside of the tube. Membrane tubes 701 are either packed with catalyst as shown in FIG. 8, or are embedded on the membrane surface as shown in FIG. 9.

Methanol, ethylene oxide and homogeneous catalyst are fed as a stream 702 in the module 700. Some fraction of the carbon dioxide is converted to products, and the flow stream 704 exits as a treated flue gas. The product stream (consisting of hydroxy-ethyl-methyl carbonate, some fraction of dimethyl carbonate and mono ethylene glycol and unreacted ethylene oxide, methanol and carbon dioxide) exits via the flow stream 705 for further conversion.

FIG. 11 is representative of an innovative concept of parallel-plate membrane module 620. Parallel plates 621 are assembled with alternate plate flow channels 623 and are packed with catalysts 622 as shown in FIG. 8. Alternatively, the catalysts 622 are embedded on the surface as shown in FIG. 9.

The carbon dioxide stream 624 enters from the side of the parallel-plate membrane module 620, as shown by FIG. 11, and exists from the other side as a flow stream 626. Flow stream 628 consisting of ethylene oxide, methanol and homogenous catalyst is introduced from the top of the module 620 and flows down through the channels 623 that hold catalysts 622. Carbon dioxide diffusing through the membrane reacts with ethylene oxide and methanol in the presence of heterogeneous catalyst 622 packed in the flow channels 623 and the homogeneous catalyst flowing with the reactants to produce hydroxy-ethyl-methyl carbonate.

The products stream 630 is withdrawn from the bottom of the membrane module 620. The elemental section of plate-and-frame membrane module 620 can be assembled in a commercial-scale unit based on the well-known technology "know how" of plate heat exchangers as exemplified in FIG. 12.

Alternatively to the design presented in FIGS. 10-12, commercial membrane modules including spiral-wound membrane modules or hollow-fiber membrane modules can also be employed. However, loading these types of commercial membranes with catalysts is difficult and such membrane modules cannot be built on a large scale required for capture and conversion of carbon dioxide from large-scale primary sources from utilities and industrial processes to alkyl carbonates.

For the process streams illustrated in FIGS. 1, 2 and 3, the methanol/dimethyl carbonate azeotrope is shown to be broken at the PerVap membrane unit in a distillate between the two distillation columns, and the recovered methanol is recycled and fed to either singular or multiple side reactors. PerVap membrane units used in the subject system may be commercially available and may include zeolite, cross-linked chitosan and highly fluorinated polymer membranes.

The PerVap membrane units presented in previous paragraphs are representative of an exemplary concept of the separation technique, and other separation techniques for separating and recycling the excess reactant methanol from the product stream may be used as well in the subject system. Such separation methods applicable in the subject system may include, for example, molecular-sieve separation, pressure-swing adsorption (PSA), temperature-swing adsorption (TSA), liquid-liquid separation of immiscible liquid mixtures, liquid entrainment and heat integrated distillation.

The side reactors, main catalytic reactor, adsorbent-catalytic reactor and membrane reactors illustrated in FIGS. 1-3 may be packed with commercial heterogeneous catalysts for either process illustrated. Alternatively, homogeneous catalysts that are soluble in methanol and referenced here may be used along with heterogeneous catalyst. Such catalysts may be used in a form of Amberlyst A21, or A26, or an alternate catalyst.

Homogeneous ionic catalysts may be Tri-methyl-butyl ammonium chloride (TMBAC), or Tri-methyl-butyl ammonium bromide (TMBAB), or Tri-ethyl-butyl ammonium bromide (TEBAB), or Tetra-butyl ammonium chloride (TBAC), or Tetra-butyl ammonium bromide (TBAB). Alkyl may be any saturated carbon chain having less than 10 carbons. Different catalysts may be also used on an individual membrane reactor, primary catalytic reactor, or an adsorbent-catalytic reactor for direct conversion, as well as the individual side reactor.

Table 1 represents process parameters for a typical commercial plant depicted in FIG. 1 with production capacity of 51,700 metric tons per year and product purity of 99 wt %. It co-produces 35,700 metric tons/year of high-value mono ethylene glycol with purity of 98 wt %. The process consumes 0.49 kg of carbon dioxide per kg of dimethyl carbonate with net emissions of 0.19 kg carbon dioxide, as shown in table below, by accounting credit for coproduction of mono ethylene glycol. If the feed stock methanol is produced by renewable hydrogen and carbon dioxide, then there would be net permanent sequestration of carbon dioxide in the form of consumer products. This is compared to emissions of 1.76 kg carbon dioxide per kg of dimethyl carbonate produced by syngas-based commercial process.

TABLE 1

Process parameters of a commercial DMC process

| Process Parameter | Value | Units |
|---|---|---|
| Dimethyl Carbonate (DMC) Production Capacity | 51,700 | Metric tons/year |
| Mono Ethylene Glycols as Coproduct Products | 35,700 | Metric tons/year |
| Dimethyl Carbonate | 6,559 | kg/hr |
| Purity | 99% | wt % |
| Mono Ethylene Glycol as Coproduct | 4,526 | kg/hr |
| Purity | 98% | |
| Feedstock | | |
| $CO_2$ feed stream - flue gas | 45,083 | kg/hr |
| $CO_2$ concentration with 60% utilization | 12% | |
| Fresh Methanol Flow Rate | 4,710 | kg/hr |
| Ethylene Oxide Flow Rate | 3,249 | kg/hr |
| Side Reactors | | |
| Temperature | 170 | ° C. |
| Pressure | 27 | bar |
| First Distillation column | | |
| Reflux Condenser/Bottom Reboiler Temperatures | 47/180 | ° C. |
| Pressure | 0.5 to 1.0 | bar |
| Second Distillation column | | |
| Reflux Condenser/Bottom Reboiler Temperatures | 47/150 | ° C. |
| Pressure | 0.5 to 1.0 | bar |

TABLE 1-continued

Process parameters of a commercial DMC process

| Process Parameter | Value | Units |
|---|---|---|
| Third Distillation column | | |
| Reflux Condenser/Bottom Reboiler Temperatures | 167/223 | ° C. |
| Pressure | 15 to 30 | bar |
| $CO_2$ Merit Value | | |
| $CO_2$ Consumed | 0.49 | kg $CO_2$/kg DMC |
| $CO_2$ Generated by the process | 0.56 | kg $CO_2$/kg DMC |
| $CO_2$ Emissions of Methanol | 0.39 | kg $CO_2$/kg DMC |
| $CO_2$ Emissions of Ethylene Oxide | 0.31 | |
| Credit for Coproduct | 0.58 | |
| Net $CO_2$ emission | 0.19 | kg $CO_2$/kg DMC |

Table 2 represents the estimated global demands of dimethyl carbonate and corresponding potential abatement of carbon dioxide emissions in 2018 and 2030. With full implementation of the subject process by 2050, there would be significant global abatement of carbon dioxide.

TABLE 2

Dimethyl carbonate market and $CO_2$ abatement potential

| | DMC Market potentials, kTA* | | $CO_2$ Abatement Potentials, kTA* | |
|---|---|---|---|---|
| Applications | 2018 | 2030 | 2018 | 2030 |
| Polycarbonate production | 2,440 | 4,910 | 3,831 | 7,708 |
| Lithium-ion batteries | 45 | 350 | 71 | 550 |
| Solvent (replacing ketones) | 1,430 | 1,430 | 2,245 | 2,857 |
| Polyurethane production | 11,350 | 11,350 | 17,820 | 28,998 |
| Diesel-engine additive** | | 1,580,000 | | 2,480,000 |

*Thousand metric tons per year
**Based on government approval for pollution control Validation of ASPEN Plus® Design Model The subject system and method enabled development of an ASPEN Plus® model for design and simulation of the dimethyl carbonate process depicted in FIGS. 1-3. The model was validated with performance data acquired using a prototype test unit shown by process diagram presented in FIG. 13. Ethylene carbonate was used as a feed for a laboratory testing since ethylene oxide is hazardous and was not to be used for laboratory tests. This prototype test unit transpires as the first column equipped with side reactors. Table 3 represents the test matrix covering process parameters typical of commercial process.

TABLE 3

Test matrix for the semi-integrated test unit

| | Feed | | | Column | Reactor Temperature | | |
|---|---|---|---|---|---|---|---|
| Test Run | g/min | EC wt % | MEG wt % | Pressure bars | SR-1 | SR-2 | SR-3 |
| DMCD01 | 40.3 | 50.9% | | 0.2 | 72.2 | 75.4 | 77.1 |
| DMCD02 | 60.2 | 49.2% | | 0.2 | 71.8 | 69.6 | 71.0 |
| DMCD03 | 39.3 | 49.1% | | 0.2 | 71.1 | 70.9 | 70.1 |
| DMCD04 | 40.6 | 50.3% | | 0.2 | 71.7 | 68.8 | 70.2 |
| DMCD05 | 42.8 | 50.1% | | 0.2 | 71.1 | 69.7 | 70.2 |
| DMCD06 | 42.2 | 48.7% | | 0.3 | 70.9 | 70.0 | 70.0 |
| DMCD07 | 40.8 | 48.7% | | 0.3 | 82.4 | 80.9 | 80.6 |
| DMCD08 | 30.9 | 51.0% | | 0.2 | 71.8 | 72.2 | 71.4 |
| DMCD09 | 30.5 | 49.4% | | 0.2 | 76.4 | 84.2 | 79.2 |
| DMCD10 | 41.1 | 47.9% | 0.04% | 0.2 | 71.1 | 71.7 | 70.0 |
| DMCD11 | 41.7 | 50.9% | 0.13% | 0.2 | 70.6 | 72.0 | 68.8 |
| DMCD12 | 40.1 | 62.9% | | 0.2 | 71.2 | 70.7 | 69.4 |
| DMCD13 | 40.6 | 48.2% | 2.00% | 0.2 | 71.1 | 70.7 | 69.0 |

The overall process parameters including experimental overhead distillate flow, bottom product flow and ethylene glycol flow, as side product, are presented in the Table 4. The measured experimental values are compared with ASPEN Plus® model predictions. Table 4 also shows experimental and predicted purity of mono ethylene glycol under different test conditions.

TABLE 4

Performance parameters of the reaction column

| | Main Column | | | | | | | |
|---|---|---|---|---|---|---|---|---|
| | Flow g/min | | | | | | | |
| | Distillate | | Bottoms | | MEG Flow g/min | | MEG Purity wt % | |
| Test Run | EXP | ASPEN | EXP | ASPEN | EXP | ASPEN | EXP | ASPEN |
| DMCD01 | 4.1 | 5.3 | 2.1 | 6.0 | 11.2 | 11.2 | 87% | 76% |
| DMCD02 | 5.7 | 5.0 | 13.6 | 17.9 | 8.8 | 8.84 | 92% | 77% |
| DMCD03 | 6.0 | 5.2 | 4.3 | 7.1 | 9.3 | 9.3 | 87% | 74% |
| DMCD04 | 7.4 | 8.2 | 9.6 | 10.7 | 5.1 | 5.1 | 92% | 94% |
| DMCD05 | 8.8 | 4.7 | 6.3 | 10.4 | 8.6 | 8.6 | 91% | 74% |
| DMCD06 | 4.2 | 4.8 | 7.0 | 9.2 | 6.8 | 6.8 | 91% | 92% |
| DMCD07 | 4.1 | 7.1 | 3.9 | 1.8 | 10.7 | 10.7 | 92% | 87% |
| DMCD08 | 2.9 | 4.9 | 1.7 | 5.0 | 7.1 | 7.1 | 91% | 94% |
| DMCD09 | 3.0 | 6.9 | 1.4 | 0.6 | 8.4 | 8.4 | 89% | 88% |
| DMCD10 | 3.3 | 3.5 | 7.5 | 9.4 | 7.7 | 7.7 | 90% | 84% |
| DMCD11 | 3.7 | 4.0 | 9.0 | 11.5 | 7.0 | 7 | 90% | 92% |
| DMCD12 | 4.0 | 4.2 | 8.3 | 14.7 | 7.8 | 7.8 | 92% | 77% |
| DMCD13 | 3.0 | 4.6 | 5.8 | 8.5 | 7.9 | 7.7 | 91% | 88% |

Validation of Side Reactors

Figure 13:
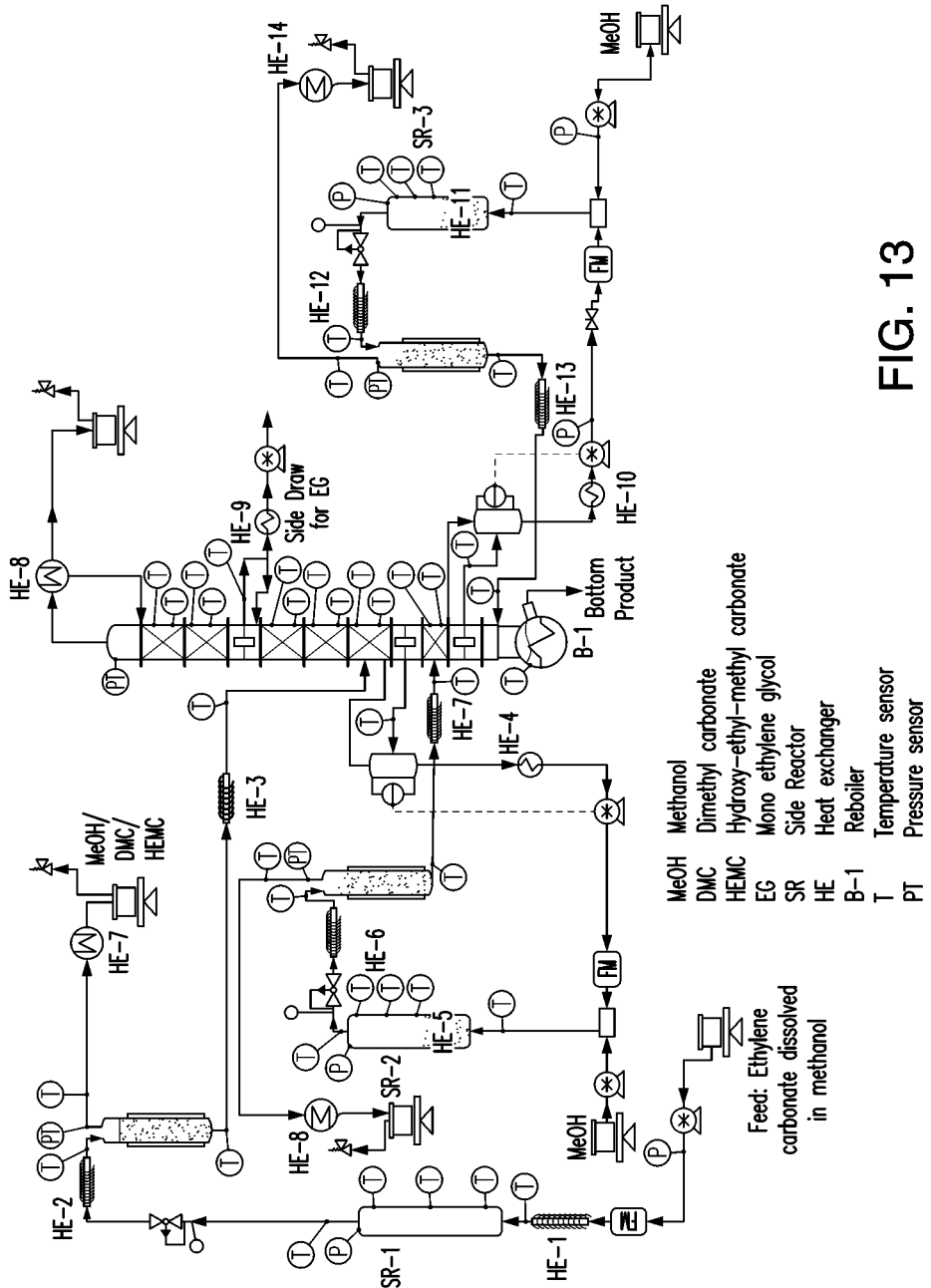
FIG. 13 is a schematic process flow diagram of the prototype test unit the performance data from which were used for validation of the ASPEN Plus® design model.

ASPEN Plus® process analysis is validated with the experimental test data obtained for individual three side reactors shown in FIG. 13. A flow redirecting device is installed in a packed column for directing a liquid flowing down the packed column to the side reactor. The vapor rising from the bottom part of the column is bypassed as the side draw line of the liquid.

The product stream from the side reactor is returned to the next stage of the packing below the point of side draw. An integrated pump and a surge tank system are used for controlling the liquid flow to the side reactor. As presented in Table 5, the ASPEN Plus® model was validated with the measured conversion of ethylene carbonate (EC) and yield of dimethyl carbonate (DMC).

TABLE 5

Conversion of ethylene carbonate (EC) and yield of dimethyl carbonate (DMC) inside reactors

| | Side Reactor Conversion | | | | | | | | | | | |
|---|---|---|---|---|---|---|---|---|---|---|---|---|
| | SR-1 | | | | SR-2 | | | | SR-3 | | | |
| | EXP | | ASPEN | | EXP | | ASPEN | | EXP | | ASPEN | |
| Test Run | EC Conv | DMC Yield | EC Conv | DMC Yield | EC Conv | DMC Yield | EC Conv | DMC Yield | EC Conv | DMC Yield | EC Conv | DMC Yield |
| DMCD01 | 59% | 28% | 50% | 24% | 46% | 16% | 36% | 10% | 33% | 17% | 38% | 12% |
| DMCD02 | 54% | 22% | 49% | 18% | 36% | 9% | 31% | 5% | 36% | 7% | 30% | 4% |
| DMCD03 | 56% | 26% | 52% | 24% | 41% | 12% | 33% | 6% | 42% | 8% | 36% | 6% |
| DMCD04 | 58% | 27% | 51% | 23% | 40% | 11% | 33% | 5% | 36% | 6% | 37% | 7% |
| DMCD05 | 56% | 23% | 49% | 19% | 38% | 8% | 35% | 6% | 47% | 10% | 42% | 8% |
| DMCD06 | 54% | 24% | 54% | 24% | 42% | 7% | 33% | 6% | 36% | 4% | 35% | 6% |
| DMCD07 | 55% | 35% | 59% | 38% | 40% | 12% | 34% | 11% | 45% | 13% | 38% | 11% |
| DMCD08 | 56% | 27% | 53% | 28% | 40% | 9% | 36% | 9% | 44% | 12% | 43% | 10% |
| DMCD09 | 59% | 36% | 55% | 34% | 44% | 17% | 36% | 15% | 55% | NA | 46% | 13% |
| DMCD10 | 54% | 25% | 51% | 23% | 33% | 8% | 31% | 7% | 36% | 5% | 38% | 8% |
| DMCD11 | 51% | 21% | 47% | 19% | 35% | 8% | 33% | 7% | 38% | 5% | 40% | 8% |
| DMCD12 | 47% | 16% | 41% | 16% | 39% | 10% | 31% | 5% | 38% | 7% | 33% | 5% |
| DMCD13 | 54% | 22% | 52% | 24% | 37% | 8% | 34% | 7% | 38% | 6% | 39% | 7% |

Performance of PerVap Membrane

Table 6 represents a summary of the performance parameters. Two series of tests were performed with liquid phase and vapor phase feed as shown in Table 6. In general high-purity methanol was separated as permeate with high-degree of selectivity. The PerVap membrane performance parameters were incorporated into the ASPEN Plus® process model.

TABLE 6

Performance parameters of PerVap membrane

| ID | Liquid Feed Rate mL/min | Feed Temp C. | Perm. Flux g/min | Composition, wt % | | | | | | Permeation Flux kg/m²/hr | MeOH/DMC Selectivity | Comments |
|---|---|---|---|---|---|---|---|---|---|---|---|---|
| | | | | Feed | | Retentate | | Permeate | | | | |
| | | | | MeOH | DMC | MeOH | DMC | MeOH | DMC | | | |
| Liquid Feed | | | | | | | | | | | | |
| TEST 1 | 4.0 | 95 | 0.51 | — | — | 67.3% | 32.7% | 95.9% | 4.1% | 6.1 | 11.4 | |
| TEST 2 | 4.0 | 95 | 1.04 | 65.0% | 35.0% | 64.9% | 35.1% | 95.5% | 4.5% | 12.5 | 11.5 | Broken O-ring |
| TEST 3 | 4.0 | 105 | 0.68 | 67.8% | 32.2% | 66.3% | 33.7% | 97.9% | 2.1% | 8.2 | 23.7 | |
| TEST 4 | 4.0 | 105 | 0.59 | 65.3% | 34.7% | 63.4% | 36.6% | 97.3% | 2.7% | 7.1 | 20.8 | |
| TEST 5 | 4.0 | 105 | 0.65 | 61.1% | 38.9% | 57.4% | 42.6% | 98.0% | 2.0% | 7.8 | 36.4 | |
| Vapor Feed | | | | | | | | | | | | |
| TEST 6 | 4.0 | 105 | 0.34 | 26.5% | 73.5% | 24.7% | 75.3% | 93.6% | 6.4% | 4.1 | 44.6 | |
| TEST 7 | 4.0 | 109 | 0.36 | 19.7% | 80.3% | 23.1% | 76.9% | 61.4% | 8.6% | 4.3 | 35.4 | |
| TEST 8 | 4.0 | 139 | 0.31 | 67.7% | 32.3% | 68.0% | 32.0% | 96.2% | 3.8% | 3.7 | 11.9 | |
| TEST 9 | 4.0 | 133 | 0.27 | 68.6% | 31.4% | 68.6% | 31.4% | 97.3% | 2.7% | 3.2 | 16.5 | |

Membrane area 0.005 m²
Selectivity, MeOH/DMC $$\alpha_{MeOH/DMC} = \frac{Y_{MeOH}/Y_{DMC}}{X_{MeOH}/X_{DMC}}$$

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method for producing a concentrated dimethyl carbonate composition and a mono-ethylene glycol co-product by a direct utilization of carbon dioxide from primary sources by eliminating the commercial process of ethylene carbonate, the method comprising:

(a) operatively coupling a reactor to a catalyst recovery unit, said reactor being selected from a group including a membrane reactor, an adsorbent catalytic reactor, a catalytic reactor, and combinations thereof;

(b) entering a carbon dioxide stream, methanol stream and ethylene oxide stream in said reactor, and reacting said carbon dioxide with said methanol and said ethylene oxide in said reactor to form hydroxy-ethyl-methyl carbonate;

(c) forming in said reactor a product stream consisting primarily of a mixture of said hydroxy-ethyl-methyl carbonate, unreacted methanol, unreacted ethylene oxide, and a low-level of dimethyl carbonate, and inserting said product stream from said reactor into said catalyst recovery unit;

(d) dissolving a homogeneous catalyst in said unreacted methanol in said catalyst recovery unit, and recycling said homogeneous catalyst dissolved in said unreacted methanol from said catalyst recovery unit to said reactor;

(e) operatively coupling a distillation sub-system to said catalyst recovery unit, said distillation sub-system including a reaction distillation column, a recycle column, and a product recovery column operatively coupled to one another;

(f) charging said reaction distillation column with said mixture of hydroxy-ethyl-methyl carbonate, unreacted ethylene oxide and unreacted methanol, and the low-level dimethyl carbonate;

(g) drawing a mixture of dimethyl carbonate, hydroxy-ethyl-methyl carbonate and unreacted methanol from at least a first stage of said reaction distillation column;

(h) operatively coupling at least a first side reactor to said first stage of said reaction distillation column, and directing said drawn mixture of dimethyl carbonate, hydroxy-ethyl-methyl carbonate and unreacted methanol through said at least first side reactor to produce a product stream containing concentrated dimethyl carbonate composition;

(i) feeding the product stream containing a concentrated dimethyl carbonate composition from said at least first side reactor to at least a first stripping column equipped with an internal reboiler for flash separation of a vapor stream of said concentrated dimethyl carbonate composition;

(j) directing said vapor stream of said concentrated dimethyl carbonate composition from said first stripping column to said recycle column;

(k) forming a liquid product stream containing unreacted hydroxy-ethyl-methyl carbonate and methanol in said first stripping column and directing said liquid product stream with unreacted hydroxy-ethyl-methyl carbonate and methanol to said reaction distillation column;

(l) forming in said reaction distillation column a bottom product containing a an unreacted hydroxy-ethylmethyl carbonate, and recycling said bottom product containing the unreacted hydroxy-ethyl-methyl carbonate from said reaction distillation column to at least a second side reactor operatively coupled to said reaction distillation column and charged with homogeneous catalysts to produce the bottom product with a concentrated unreacted hydroxy-ethyl-methyl carbonate and homogeneous catalysts;

(m) forming in said reaction distillation column an overhead stream containing unreacted methanol;

(n) operatively coupling at least a first Permeation-Vaporization (PerVap) membrane to said reaction distillation column, and condensing and feeding said overhead stream from said reaction distillation column to said at least first PerVap membrane for selective separation of a methanol retentate from said overhead stream for recycling, (o) feeding said retentate from said at least first PerVap to said recycle column;

(p) recycling said bottom product containing the concentrated unreacted hydroxy-ethyl-methyl carbonate and homogeneous catalysts to said recycle column, and producing an overhead stream therein, said overhead stream containing an unreacted methanol;

(q) operatively coupling at least a second PerVap membrane to said recycle column, and feeding said overhead stream from said recycle column to said at least second PerVap membrane for condensing and selective separation of the unreacted methanol as permeate from said overhead stream for recycle, thus producing a further concentrated dimethyl carbonate and methanol composition;

(r) feeding said retentate from said at least second PerVap membrane to said product recovery column operated at an elevated pressure, and forming in said product recovery column an overhead stream containing an unreacted methanol and a bottom product stream containing dimethyl carbonate (DMC);

(s) condensing said overhead stream from said product recovery column to separate a methanol permeate therefrom and feeding said separated methanol permeate into a storage vessel for recycling said methanol retentate; and (t) recovering a high-purity dimethyl carbonate (DMC) from said bottom product stream of said product recovery column.

2. The method as recited in claim 1, wherein said reaction distillation column is configured with a structure selected from a group including a sieve tray, packed thermally active trays and packings disposed at predetermined locations, and combinations thereof.

3. The method as recited in claim 1, further comprising: operating said membrane reactor to dilute said carbon dioxide stream,
wherein said membrane reactor includes a structure selected from a group including:
membrane modules with catalysts packed in flow passages, catalysts embedded on a membrane surface for conversion of carbon dioxide to hydroxy-ethyl-methyl carbonate by reacting with ethylene oxide and methanol, and combination thereof.

4. The method as cited in claim 2, further comprising: capturing a high-purity carbon dioxide from combustion flue gases, via industrial processes, including ethanol fermentation process, and
feeding the high-purity carbon dioxide in said catalytic reactor.

5. The method as recited in claim 4, wherein said catalytic reactor is selected from a group of reactors including: a trickle-bed reactor, a packed-bed up-flow reactor, a fluidized-bed reactor, and combinations thereof, operating to convert said captured high-concentration carbon dioxide to hydroxyl-ethyl-methyl carbonate by reacting with ethylene oxide and methanol.

6. The method as recited in claim 1, further comprising: feeding the carbon dioxide from a primary dilute stream to said adsorbent reactor,
wherein said adsorbent reactor includes a substance selected from a group including: a solid adsorbent for capturing carbon dioxide from primary sources, a catalyst for conversion of the carbon dioxide captured on the solid adsorbent to hydroxy-ethyl-methyl carbonate by reacting with streams of ethylene oxide and methanol, homogeneous catalyst, heterogeneous catalyst, and combinations thereof.

7. The method sited in claim 6, where said homogeneous catalyst is selected from a group including: commercial tri-methyl butyl ammonium bromide (TMBAB), tri-ethyl butyl ammonium bromide (TEBAB), tri-methyl butyl ammonium chloride (TMBAC), tri-ethyl butyl ammonium chloride (TEBAC), tetra-butyl ammonium bromide (TBAB), tetra-butyl ammonium chloride (TBAC), an ionic catalyst, wherein said heterogenous catalyst is selected form a group of commercial Amberlyst A21, A26, transesterification catalyst, and combinations thereof.

8. The method is recited in claim 1, further comprising: recovering and recycling homogeneous catalysts from said product stream routed from said reactor through said catalyst recovery unit.

9. The method as recited in claim 1, wherein said at least second side reactor is operatively coupled to a bottom stream of the reaction distillation column for further conversion of the concentrated hydroxy-ethyl-methyl carbonate in said bottom product to said concentrated dimethyl carbonate composition.

10. The method as recited in claim 9, further comprising: in said step (h), charging the unreacted hydroxy-ethyl-methyl carbonate into said reaction distillation column below a location in said reaction distillation column where the drawn mixture is passed to said at least at least first side reactor.

11. The method as recited in claim 9, further comprising: operatively coupling at least a second stripping column to said at least second side reactor, and
feeding the concentrated vapor streams containing dimethyl carbonate from each of said first and second stripping columns connected to sad at least first and second side reactors, respectively, to said recycle column for further concentration of dimethyl carbonate and recycling of the unreacted hydroxy-ethyl-methyl carbonates an methanol.

12. The method as recited in claim 9, further comprising: following said step (k) of returning of a mixture of said unreacted hydroxy-ethyl-methyl carbonate and methanol to said reaction distillation column, passing said mixture through a plurality of distillation stages in said reaction distillation column in the direction to a lower section of said reaction distillation column.

13. The method as recited in claim 1, further including: feeding multiple streams including said vapor stream of said concentrated dimethyl carbonate composition from said first stripping column, said methanol permeate from said at least first PerVap, and said bottom product containing the concentrated unreacted hydroxy-ethyl-methyl carbonate and homogeneous catalysts, in said steps (j), (o), and (p), respectively, to said recycle column for further concentration of the dimethyl carbonate composition and recovering and recycling of the unreacted hydro-ethyl-methyl carbonate dissolved in methanol.

14. The method as recited in claim 13, further comprising:
operatively interlinking at least a third PerVap membrane with said product recovery column, passing the concentrated dimethyl carbonate composition in vapor phase through said at least third PerVap membrane and returning to said product recovery column for recovery of high concentration dimethyl carbonate.

15. The method as recited in claim 1, further comprising a further concentration of dimethyl carbonate and unreacted methanol composition in said recycle column by the steps of:
in said step (g), removing said dimethyl carbonate and unreacted methanol composition from an upper section of the reaction distillation column;
in said step (h), directing said concentrated dimethyl carbonate and unreacted methanol composition through said at least first PerVap membrane, and separating said concentrated dimethyl carbonate from said unreacted methanol of said composition in said at least first PerVap membrane, thus further concentrating the dimethyl carbonate stream; and
in said step (j), returning said further concentrated stream of dimethyl carbonate to a middle section of said recycle column.

16. The method as recited in claim 1, further comprising a further concentration of the dimethyl carbonate composition in said product recovery column through the steps of:
in said step (h), removing said further concentrated dimethyl carbonate and methanol composition from an upper section of the recycle column;
separating said dimethyl carbonate and methanol composition in said at least second PerVap membrane;
returning said concentrated stream of dimethyl carbonate from said recycle column to an upper section of said product recovery column;
interlinking at least a third PerVap membrane to said product recovery column, passing said dimethyl carbonate and methanol composition through said at least third membrane, thus selectively separating methanol and obtaining a further concentrated dimethyl carbonate, and
returning the further concentrated dimethyl carbonate to said product recovery column.

17. The method as recited in claim 16, further comprising:
recovering heat from said upper section of said product recovery column and transmitting said recovered heat to said at least first, second and third PerVap membranes and to at least one of said reaction distillation and recycle columns; and
in said step (t), recovering the high-concentration dimethyl carbonate as said bottom product.

18. The method as recited in claim 17, wherein the step of concentrating dimethyl carbonate in said product recovery column further includes the steps of:
withdrawing a side stream from one of the stages of the said product recovery column;
feeding said side stream into said at least second PerVap membrane for selective separation of methanol from azeotropic mixture of dimethyl carbonate and methanol, thus obtaining a retentate stream of a concentrated dimethyl carbonate stream; and
returning said retentate stream of concentrated dimethyl carbonate stream to said upper stage of said product recovery column.

19. The method as recited in claim 16, wherein said at least first, second and third PerVap membranes selectively separate methanol from azeotropic mixture of dimethyl carbonate and methanol.

20. The method as recited in claim 17, wherein said recovered heat is transmitted via a liquid or vapor phase heat transfer media by employing a compact heat transfer device or a heat pipe.

\* \* \* \* \*